United States Patent
Lewis et al.

(10) Patent No.: US 7,507,717 B2
(45) Date of Patent: Mar. 24, 2009

(54) TYPE II CHI-CONOTOXIN PEPTIDES (NORADRENALINE TRANSPORTER INHIBITORS)

(75) Inventors: Richard James Lewis, Woolloongabba (AU); Paul Francis Alewood, Pullenvale (AU); Dianne Alewood, Pullenvale (AU); Elka Palant, Kenmore (AU)

(73) Assignee: Xenome Ltd., Queensland (AU)

( * ) Notice: Subject to any disclaimer, the term of this patent is extended or adjusted under 35 U.S.C. 154(b) by 87 days.

(21) Appl. No.: 10/537,088

(22) PCT Filed: Dec. 2, 2003

(86) PCT No.: PCT/AU03/01606

§ 371 (c)(1),
(2), (4) Date: Dec. 27, 2005

(87) PCT Pub. No.: WO2004/050688

PCT Pub. Date: Jun. 17, 2004

(65) Prior Publication Data

US 2006/0270832 A1 Nov. 30, 2006

Related U.S. Application Data

(60) Provisional application No. 60/430,307, filed on Dec. 2, 2002.

(51) Int. Cl.
   *A61K 38/04* (2006.01)
   *A61K 38/08* (2006.01)
   *C07K 7/06* (2006.01)
   *C07K 7/08* (2006.01)

(52) U.S. Cl. .......................... 514/14; 514/15; 530/327; 530/328

(58) Field of Classification Search .................. 514/14, 514/15; 530/327, 328
See application file for complete search history.

(56) References Cited

U.S. PATENT DOCUMENTS 5,587,454 A    12/1996  Justice et al.

(Continued)

FOREIGN PATENT DOCUMENTS

WO        WO 91/07980        6/1991

(Continued)

OTHER PUBLICATIONS

Takagi, H. et al., "Analgesic Effect of L-threo-3-4-dihydroxyphenylserine (L-DOPS) in Patients with Chronic Pain", European Neuropsychopharmacology, 6: 43-47 (1996).

(Continued)

*Primary Examiner*—Rebecca E. Prouty
*Assistant Examiner*—Rosanne Kosson
(74) *Attorney, Agent, or Firm*—Scully, Scott, Murphy & Presser, P.C.

(57) ABSTRACT

An isolated, synthetic or recombinant X-conotoxin peptide having the ability to inhibit neuronal amine transporter comprising the following sequence of amino acids: Cys Cys Gly Tyr Lys Leu Cys Xaa5 Xaa6 Cys, SEQ ID NO:3, where Xaa5 and Xaa6 are independently absent or represent any amino acid residue except Cys; or a sequence in which Gly, Tyr, Lys or Leu are subject to conservative amino acid substitution or side chain modification with the proviso that the peptide is not MrIA, MrIB, Mar2, CMrVIA, Bn1.5, Mr1.3 or Au1.4; or a salt, ester, amide, prodrug or cyclised derivative thereof.

16 Claims, 1 Drawing Sheet

U.S. PATENT DOCUMENTS

| | | | |
|---|---|---|---|
| 6,767,896 | B1 | 7/2004 | McIntosh et al. |
| 6,794,361 | B1 | 9/2004 | Lewis et al. |
| 2003/0109670 | A1* | 6/2003 | Olivera et al. ............... 530/324 |
| 2005/0054827 | A1 | 3/2005 | Lewis et al. |

FOREIGN PATENT DOCUMENTS

| | | |
|---|---|---|
| WO | WO 96/14079 | 5/1996 |
| WO | WO 96/40064 | 12/1996 |
| WO | WO 97/01351 | 1/1997 |
| WO | WO 97/30997 | 8/1997 |
| WO | WO 98/02148 | 1/1998 |
| WO | WO 98/05309 | 2/1998 |
| WO | WO 98/22126 | 5/1998 |
| WO | WO 98/51668 | 11/1998 |
| WO | WO 00/20444 | 4/2000 |
| WO | WO 00/44769 | 8/2000 |

OTHER PUBLICATIONS

Eisenach, C. et al., "Cerebrospinal Fluid Norepinephrine and Acetylcholine Concentrations During Acute Pain", Anesth Analg, 82: 621-626 (1996).

Dubner, R. et al., "The Neurobiology of Pain and Its Modulation", The Clinical Journal of Pain, 5(Suppl 2): S1-S6 (1989).

Dyck, P.J. et al., "New Understanding and Treatment of Diabetic Neuropathy", The New England Journal of Medicine, 326(19):1287-1288 (1992).

Atkinson, J. H. et al., "A Placebo-controlled Randomized Clinical Trial of Nortriptyline for Chronic Low Back Pain", Pain, 76: 287-296 (1998).

Springer, J. P. et al., "Facilitatory and Inhibitory Effects of Selective Norephinephrine Reuptake Inhibitors on Hypogastric Nerve-Evoked Urethral Contractions in the Cat: A Prominent Role of Urethral $-Adrenergic Receptors", The Journal of Urology, 152: 515-519 (1984).

Dinan, T. G. et al., "Assessment of Central Noradrenergic Functioning in Irritable Bowel Syndrome Using a Neuroendocrine Challenge Test", Journal of Psychosomatic Research, 34(5): 575-580 (1990).

Leung, D. et al., "Protease Inhibitors: Current Status and Future Prospects", J. Med Chem, 43(3): 305-341 (2000).

O'Neill, M. J. et al., "Effects of $Ca^{2+}$ and $Na^+$ channel inhibitors in vitro and in global cerebal ischaemia in vivo", European Journal of Pharmacology, 332: 121-131 (1997).

Eisenach, J. C. et al., "Intrathecal, but Not Intravenous, Clonidine Reduces Experimental Thermal or Capsaicin-Induced Pain and Hyperalgesia in Normal Volunteers", Anesth Analg, 87: 591-596 (1998).

Marban, E. et al., "Structure and Function of Voltage-Gated Sodium Channels", Journal of Physiology, 508.3: 647-657 (1998).

Yanagawa, Y. et al., "A Novel Sodium Channel Inhibitor from Conus geographus: Purification, Structure, and Pharmacological Properties", Biochemistry, 27: 6256-6262 (1988).

Ryan, R., et al., "Evaluation of an Enkephalin Analog in Men with Castor Oil-Induced Diarrhea", Clinical Pharmacol Ther, 39(1): 40-42 (1986).

Penttila, O, et al., "Studies of Rectal Mucosal Catecholamines in Ulcerative Colitis", Annals of Clinical Resarch, 7: 32-36 (1975).

Bowersox, S.S. et al., "Selective N-Type Neuronal Voltage-Sensitive Calcium Channel Blocker, SNX-111, Produces Spinal Antinociception in rat Models of Acute, Persistent and Neuropathic Pain", J. Pharmacol Exp. Ther., 279 (3): 1243-1249 (1996).

Krames, Elliot S. et al., "Intrathecal D-Ala2-D-Leu5-enkephalin (DADL) Restores Analgesia in a Patient Analgetically Tolerant to Intrathecal Morphine Sulfate", Pain, 24: 205-209 (1986).

* cited by examiner

Figure 1: Anti-allodynic effects of (A) i.t. SEQ ID NO 20 and (B) MrIA in Chronic Constriction Injury (CCI) of the rat sciatic nerve
A.
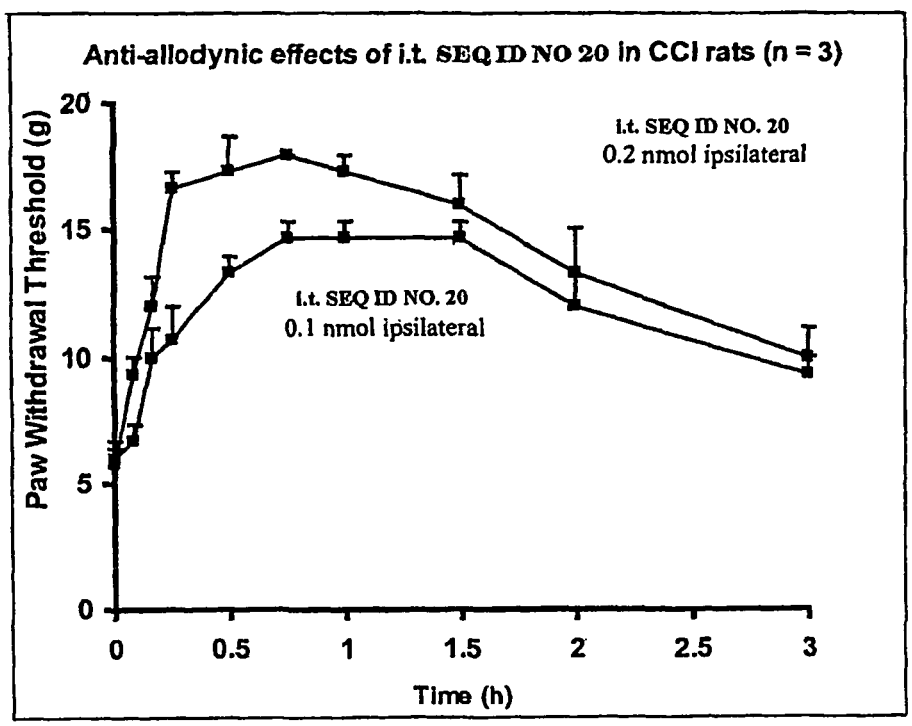
B.
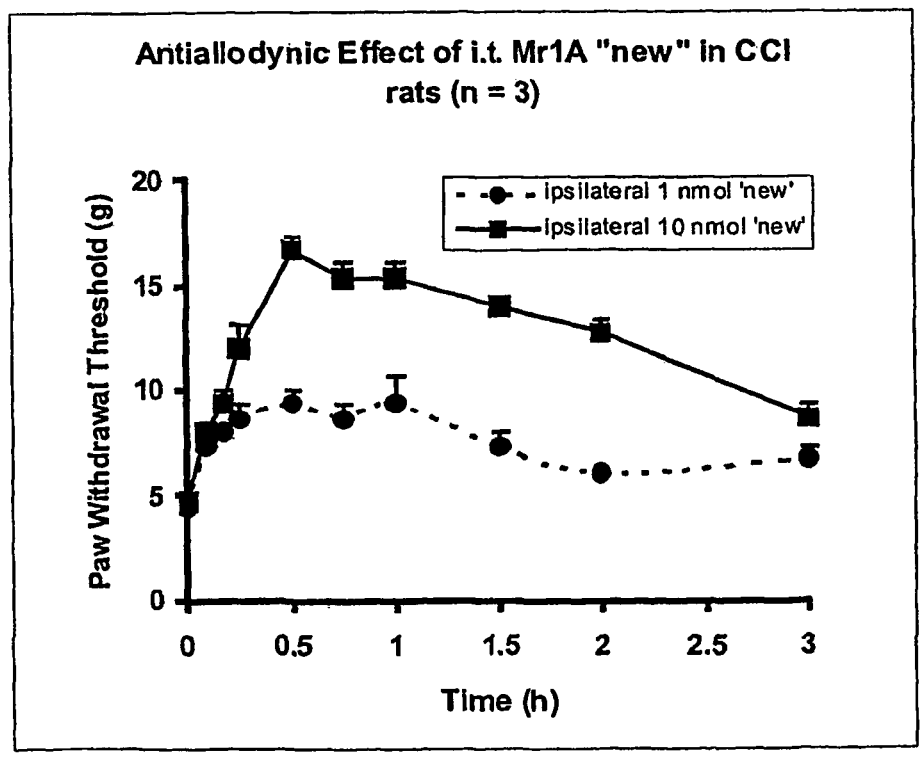

TYPE II CHI-CONOTOXIN PEPTIDES (NORADRENALINE TRANSPORTER INHIBITORS)

CROSS REFERENCE TO RELATED APPLICATIONS

This application is the §371 national phase of PCT/AU2003/001606, filed on Dec. 2, 2003, which claims priority from U.S. Provisional Application No. 60/430,307, filed on Dec. 2, 2002.

The present invention relates to novel χ-conotoxin peptides useful as inhibitors of neuronal amine transporters of neurotransmitters, such as noradrenaline, serotonin, dopamine, glutamic acid and glycine. The invention also relates to pharmaceutical compositions comprising these peptides and the use of these peptides in the prophylaxis or treatment of conditions, such as but not limited to, pain, inflammation, incontinence, cardiovascular conditions and mood disorders.

The marine snails of the genus *Conus* (cone snails) use a sophisticated biochemical strategy to capture their prey. As predators of either fish, worms or other molluscs, the cone snails inject their prey with venom containing a cocktail of small bioactive peptides. These toxin molecules, which are referred to as conotoxins, interfere with neurotransmission by targeting a variety of receptors and ion-channels. The venom from any single *Conus* species may contain more than 100 different peptides. The conotoxins are divided into classes on the basis of their physiological targets. The ω-conotoxin class of peptides target and block voltage-sensitive $Ca^{2+}$-channels inhibiting neurotransmitter release. The α-conotoxins and ψ-conotoxins target and block nicotinic ACh receptors, causing ganglionic and neuromuscular blockade. Peptides of the μ-conotoxin class act to block voltage-sensitive $Na^+$-channels inhibiting muscle and nerve action potentials. The δ-conotoxins target and delay the inactivation of voltage-sensitive $Na^+$-channels, enhancing neuronal excitability. The κ-conotoxin class of peptides target and block voltage-sensitive $K^+$-channels, and these also cause enhanced neuronal excitability. The conopressins are vasopressin receptor antagonists and the conantokins are NMDA receptor antagonists. The γ-conotoxin class targets a voltage-sensitive nonspecific cation channel. The σ-conotoxin class antagonises the $5HT_3$ receptor and the χ-conotoxin class inhibits neuronal amine transporters.

The χ-conotoxin class of peptides was first described in WO00/20444 (University of Queensland), although two members of the class were subsequently referred to in WO00/44769 (University of Utah Research Foundation). The particular χ-conotoxin peptides identified in WO 00/20444 were MrIA and MrIB which have the following sequences:

```
χ-MrIA  Asn Gly Val Cys Cys Gly Tyr Lys Leu Cys His Hyp Cys   SEQ ID NO. 1
χ-MrIB  Val Gly Val Cys Cys Gly Tyr Lys Leu Cys His Hyp Cys   SEQ ID NO. 2
```

In these and following sequences Hyp refers to 4-hydroxy proline. In nature, this amino acid residue results from post translational modification of the encoded peptide and is not directly encoded by the nucleotide sequence.

Additional χ-conotoxin peptides have also now been described by Balaji et al. (2000 J. Biol. Chem. 27539516-39522), McIntosh J et al. (WO00/44769). These peptides, Mar2, CMrVIA and CMRx (or UO36), have the following sequences:

```
Mar2    Gly Val Cys Cys Gly Tyr Lys Leu Cys Cys His Hyp Cys   SEQ ID NO. 7
CMrVIA  Val Cys Cys Gly Tyr Lys Leu Cys His Hyp Cys           SEQ ID NO. 8
CMRx    Gly Ile Cys Cys Gly Val Ser Phe Cys Tyr Hyp Cys       SEQ ID NO. 9
```

Other II-type conotoxin peptides have been described by Olivera et al. (WO02/064740) although the disulphide connectivity and activity of these peptides does not appear to be described. Some of those peptides are as follows:

```
Bn1.5  Ala Cys Cys Gly Tyr Lys Leu Cys Ser Pro Cys#       SEQ ID NO. 10
Mr1.3  Asn Gly Val Cys Cys Gly Tyr Lys Leu Cys Leu Pro Cys^  SEQ ID NO. 11
Au1.4  Ser Val Cys Cys Gly Tyr Lys Leu Cys Phe Pro Cys^   SEQ ID NO. 12
```

The '^' indicates that the C-terminus is preferably free carboxyl and '#' indicates that it is preferably amidated.

Compounds which inhibit neurotransmitter reuptake have been found to be useful in the treatment of acute, chronic and/or neuropathic pain, migraine and inflammation. Such compounds can also be administered with other agents useful in these treatments to provide improved pain/inflammation relief and/or reduce the severity of unwanted side effects, such as nausea and stomach upset. They have also been found to be useful in the treatment of lower urinary tract disorders, such as urinary incontinence, detrusor instability and interstitial cystitis. One such compound is "imipramine" which, in addition to inhibiting noradrenaline reuptake, has been shown to affect calcium channel blockade, and to exhibit anticholinergic activity, local anaesthetic activity and a number of other effects. Other compounds capable of inhibiting noradrenaline reuptake are described in U.S. Pat. No. 5,441,985. These compounds are said to have a reduced anticholinergic effect relative to imipramine.

In the case of the peptides of the present invention this inhibition of neurotransmitter reuptake is achieved by selectively inhibiting the neuronal neurotransmitter transporter, such as the noradrenaline transporter, which functions to rapidly clear released noradrenaline from the synapse back into neurons.

As described in WO00/20444, the peptides χ-MrIA and χ-MrIB are composed of a tail, residues 1-3, two loops, residues 6-9 (loop 1) and 11-12 (loop 2), respectively and two disulfide bonds between cysteine residues 4 and 13 and 5 and 10, respectively. While MrIA resembles a α-conotoxin peptide in terms of the number of cysteine residues, the disulfide connectivity is different. In this regard the α-conotoxin peptides are characterised by an A-C/B-D connectivity, rather than the A-D/B-C connectivity of MrIA, where A, B, C and D represent the first, second, third and fourth cysteine residues involved in disulfide bond formation respectively.

It has now been found that a particular part of the MrIA sequence is essential for the biological activity, and that the activity of MrIA can be enhanced by making particular modifications to its primary structure.

Accordingly in a first aspect the present invention there is provided an isolated, synthetic or recombinant χ-conotoxin peptide having the ability to inhibit neuronal amine transporter comprising the following sequence of amino acids:

```
                                           SEQ ID NO. 3
    Cys Cys Gly Tyr Lys Leu Cys Xaa5 Xaa6 Cys
``` where Xaa5 and Xaa6 are independently absent or represent any amino acid residue except Cys, or such a sequence in which Gly, Tyr, Lys or Leu are subject to conservative amino acid substitution or side chain modification, with the proviso that the peptide is not χ-MrIA, χ-MrIB, Mar2, CMrVIA, Bn1.5, Mr1.3 or Au1.4; or a salt, ester, amide, prodrug or cyclised derivative thereof.

It has also been found that the introduction of an additional amino acid residue at the N-terminus can increase the binding affinity of the peptide for the human noradrenaline transporter.

In a second aspect the present invention provides an isolated, synthetic or recombinant α-conotoxin peptide having the ability to inhibit neuronal amine transporter comprising the following sequence of amino acids:

```
Xaa1 Xaa2 Xaa3 Xaa4 Cys Cys Gly Tyr Lys Leu Cys Xaa5 Xaa6 Cys   SEQ ID NO. 4
``` where
  Xaa1 is selected from Trp, DTrp, Tyr, Phe, hPhe, Ala, MeY, Arg, Ben, Nap, Orn, pGlu, DpGlu and a deletion;
  Xaa2 is selected from Arg, Ala, Asn, Lys, Phe, BHK, Orn, Lys, DArg, Nle, DLys, DMK, DAsn, Thr, ABZ, Nap, Cit, Val, Tyr, Trp, pGlu, DpGlu or a deletion;
  Xaa3 is selected from Gly, Asp, Lys, Arg, Ala, Ne, Ser or Phe;
  Xaa4 is selected from Val, Leu, Nle, Ile, Thr, Ala, Asn, Trp, Phe and Abu, and
  Xaa5 and Xaa6 are as defined above, or such a sequence where one or more of the loop 1 residues Gly, Tyr, Lys and Leu are subject to conservative amino acid substitution or side chain modification, with the proviso that the peptide is not χ-MrIA, χ-MrIB, Mar2, Mr1.3 or Au1.4; and or a salt, ester, amide, prodrug or cyclised derivative thereof.

In a third aspect the present invention provides an isolated, synthetic or recombinant χ-conotoxin peptide having the ability to inhibit neuronal amine transporter comprising the following sequence of amino acids:

```
Xaa1 Xaa2 Xaa3 Xaa4 Cys Cys Gly Tyr Lys Leu Cys Xaa5 Xaa6 Cys   SEQ ID NO. 4
``` where
  Xaa1 is selected from Trp, Tyr, Phe, hPhe, Ala, MeY, Arg, Ben and Nap,
  Xaa2 is selected from Arg, Asn, Lys, BHK, Orn, Lys, DArg, Me, DLys, DMK, DAsn, Thr, ABZ, Nap, Cit and Val,
  Xaa3 is selected from Gly, Asp, Lys, Arg, Ala, Nle and Ser,
  Xaa4 is selected from Val, Leu, Nle, Ile, Thr, Ala and Abu, and
  Xaa5 and Xaa6 are as defined above, or such a sequence where one or more of the loop 1 residues Gly, Tyr, Lys and Leu are subject to conservative amino acid substitution or side chain modification, or a salt, ester, amide, prodrug or cyclised derivative thereof.

In a fourth aspect the present invention provides an isolated, synthetic or recombinant χ-conotoxin peptide having the ability to inhibit neuronal amine transporter consisting of the following sequence of amino acids:

```
Xaa1 Xaa2 Xaa3 Xaa4 Cys Cys Gly Tyr Lys Leu Cys Xaa5 Xaa6 Cys   SEQ ID NO. 4
``` where
- Xaa1 is selected from Trp, Tyr, Phe, hPhe, Ala, MeY, Arg, Ben and Nap,
- Xaa2 is selected from Arg, Asn, Lys, BHK, Orn, Lys, DArg, Nle, DLys, DMK, DAsn, Thr, ABZ, Nap, Cit and Val,
- Xaa3 is selected from Gly, Asp, Lys, Arg, Ala, Nle and Ser,
- Xaa4 is selected from Val, Leu, Nle, Ile, Thr, Ala and Abu, and
- Xaa5 and Xaa6 are as defined above, or such a sequence where one or more of the loop 1 residues Gly, Tyr, Lys and Leu are subject to conservative amino acid substitution or side chain modification or a salt, ester, amide or prodrug thereof.

It has further been found that the introduction of an N-terminally blocked residue can provide a number of advantages over MrIA.

Accordingly in a fifth aspect of the present invention there is provided an isolated, synthetic or recombinant χ-conotoxin peptide comprising the following sequence of amino acids:

The peptides according to the fifth and sixth aspects of the present invention may have a number of advantages over MrIA. A peptide of this aspect of the invention was found to have a duration of effect which extended beyond 24 hours following a bolus 30 nmol dose given i.t. Another peptide of the invention had an increase in potency of over 50-fold relative to MrIA. These peptides have also been found to be particularly stable to storage in the pH range of 4 to 7 and 37EC, allowing long term delivery in a device, for example an infusion pump, held at room temperature to 37EC. There are also advantages in relation to the production and separation of the peptides from unwanted bi-products of synthesis, allowing straightforward purification to homogeneity of >99%, relative to MrIA using a similar procedure in which purity is typically <93%.

It has further been found that the binding affinity of the χ-peptides according to the invention can be increased by introduction of particular residues at the N-terminus.

```
Xaa1 Xaa2 Xaa3 Xaa4 Cys Cys Gly Tyr Lys Leu Cys Xaa5 Xaa6 Cys    SEQ ID NO. 5
``` where
- Xaa1 is an N-terminal residue and is selected from pGlu, DpGlu, Pro, Hyp or an N-acetylated amino acid residue;
- Xaa2 is selected from Arg, Asn, Lys, BHK, Orn, Lys, DArg, Nle, DLys, DMK, DAsn, Thr, ABZ, Nap, Cit, Val and a deletion, Accordingly a seventh aspect the present invention provides an isolated, synthetic or recombinant χ-conotoxin peptide having the ability to inhibit neuronal amine transporter comprising the following sequence of amino acids:

```
                Xaa2 Xaa3 Xaa4 Cys Cys Gly Tyr Lys Leu Cys Xaa5 Xaa6 Cys    SEQ ID NO. 6
```

- Xaa3 is selected from Gly, Asp, Lys, Arg, Ala, Nle and Ser,
- Xaa4 is selected from Val, Leu, Nle, Ile, Thr, Ala and Abu, and
- Xaa5 and Xaa6 are as defined above, or such a sequence where one or more of the loop 1 residues Gly, Tyr, Lys and Leu are subject to conservative amino substitution or sidechain modification, or a salt, ester, amide or prodrug thereof.

In a sixth aspect the present invention provides an isolated, synthetic or recombinant χ-conotoxin peptide consisting of the following sequence of amino acids:

where Xaa2 is BHK, Orn, Arg, DArg or DMK and Xaa3, Xaa4, Xaa5 and Xaa6 are as defined above, or such a sequence where one or more of the loop 1 residues Gly, Tyr, Lys and Leu are subject to conservative amino acid or side chain modification, or a salt, ester, amide, prodrug or cyclised derivative thereof.

In an eighth aspect the present invention provides an isolated, synthetic or recombinant χ-conotoxin peptide having the ability to inhibit neuronal amine transporter consisting of the following sequence of amino acids:

```
Xaa1 Xaa2 Xaa3 Xaa4 Cys Cys Gly Tyr Lys Leu Cys Xaa5 Xaa6 Cys    SEQ ID NO. 5
``` where
- Xaa1 is an N-terminal residue and is selected from pGlu, Pro, Hyp or an N-acetylated amino acid residue;
- Xaa2 is selected from Arg, Asn, Lys, BHK, Orn, Lys, DArg, Nle, DLys, DMK, DAsn, Thr, ABZ, Nap, Cit, pGlu, Val and a deletion,
- Xaa3 is selected from Gly, Asp, Lys, Arg, Ala, Nle and Ser,
- Xaa4 is selected from Val, Leu, Nle, Ile, Thr, Ala and Abu, and
- Xaa5 and Xaa 6 are as defined above, or such a sequence where one or more of the loop 1 residues Gly, Tyr, Lys and Leu are subject to conservative amino and substitution or said chain modification, or a salt or prodrug thereof.

```
Xaa2 Xaa3 Xaa4 Cys Cys Gly Tyr     SEQ ID NO. 6
Lys Leu Cys Xaa5 Xaa6 Cys
``` where Xaa2 is BHK, Orn, Arg, DArg or DMK and Xaa3, Xaa4, Xaa5 and Xaa6 are as defined above, or such a sequence where one or more of the loop 1 residues Gly, Tyr, Lys and Leu are subject to conservative amino acid or side chain modification, or a salt, ester, amide, prodrug or cyclised derivative thereof.

In SEQ ID NO. 4 Xaa1 is preferably Trp, Tyr or hPhe. More preferably Xaa1 is Trp.

In SEQ ID NO. 5 Xaa1 is preferably pGlu.

In SEQ ID NO. 4 Xaa2 is preferably Arg, Lys or Asn.

In SEQ ID NO. 5 Xaa2 is preferably a deletion.

In SEQ ID NO. 6 Xaa2 is preferably BHK or Orn.

In SEQ ID NOS. 4, 5 and 6 Xaa3 is preferably Gly or Asp. More preferably Xaa3 is Gly.

In SEQ ID NOS. 4, 5 and 6 Xaa4 is preferably Leu, Nle or Val.

In SEQ ID NOS, 3, 4, 5 and 6 the following preferred definitions apply for Xaa5 and Xaa6:

Preferably Xaa5 is selected from His, Arg, Trp, Nal, Glu and a deletion. More preferably Xaa5 is Arg or His.

Xaa6 is selected from Hyp, Pro, Ala, Tic, Pip, MeY, DMD, Phe, THZ, Glu, Nle, Tyr and a deletion. More preferably Xaa6 is Hyp or Pro.

Preferably, the neuronal amine transporter is the neuronal noradrenaline transporter.

The χ-conotoxin peptide may be naturally occurring peptides isolated from a cone snail, or derivatives or synthetic versions thereof.

Preferably, the χ-conotoxin peptide is a selective inhibitor of the neuronal noradrenaline transporter. The terms "selective" and "selectively" as used herein mean that the activity of the peptide as an inhibitor of neuronal noradrenaline transporter is considerably greater than any activity at the $\alpha_1$-adrenoceptors. Preferably the peptide inhibitor is 10-fold more selective towards the neuronal noradrenaline transporter, more preferably 100-fold more selective and most preferably more than 1000-fold more selective. The peptide is also preferably selective over $\alpha_2$-adrenoceptors and/or serotonin reuptake transporter (SERT) The selectivity of an inhibitor of the neuronal noradrenaline transporter can be measured using techniques known in the art, for example using appropriate labelled ligand displacement assays.

U.S. Pat. No. 5,441,985 indicates that inhibitors of noradrenaline reuptake which have a negligible anticholinergic effect are particularly useful in the treatment of lower urinary tract disorders. It has been found that the peptides of this invention also have no detectable or substantially no detectable anticholinergic effect.

Accordingly in a preferred embodiment of the invention the χ-conotoxin peptide has the ability to selectively inhibit neuronal noradrenaline transporter, and has negligible or no substantial anticholinergic effect.

The peptides of the present invention preferably have no activity as a sodium channel blocker or as an inhibitor of dopamine transporter. The absence, in the peptides of the invention and in particular the preferred peptides according to the invention, of these additional pharmacological activities commonly associated with other noradrenaline transporter inhibitors makes these peptides useful pharmacological tools.

The peptides according to the present invention may be termed derivatives of MrIA.

The term "derivative" as used herein in connection with a naturally occurring χ-conotoxin peptide, such as χ-MrIA, refers to a peptide which differs from the naturally occurring peptides by one or more amino acid deletions, additions, substitutions, or side-chain modifications. All such derivatives of χ-MrIA according to the present invention have the ability to inhibit the neuronal noradrenaline transporter.

Substitutions encompass amino acid alterations in which an amino acid is replaced with a different naturally-occurring or a non-conventional amino acid residue. Such substitutions may be classified as "conservative", in which case an amino acid residue contained in a polypeptide is replaced with another naturally-occurring amino acid of similar character either in relation to polarity, side chain functionality or size, for example Ser⇌Thr⇌Pro⇌Hyp⇌Gly⇌Ala, Val⇌Ile⇌Leu, His⇌Lys⇌Arg, Asn⇌Gln⇌Asp⇌Glu or Phe⇌Trp⇌Tyr. It is to be understood that some non-conventional amino acids may also be suitable replacements for the naturally occurring amino acids. For example Lys residues may be substituted by ornithine, homoarginine, nor-Lys, N-methyl-Lys, N,N-dimethyl-Lys and N,N,N-trimethyl-Lys. Lys residues can also be replaced with synthetic basic amino acids including, but not limited to, N-1-(2-pyrazolinyl)-Arg, 2-(4-piperinyl)-Gly, 2-(4-piperinyl)-Ala, 2-[3-(2S)pyrrolininyl]-Gly and 2-[3-(2S)pyrolininyl]-Ala. Tyr residues may be substituted with 4-methoxy tyrosine (MeY), meta-Tyr, ortho-Tyr, nor-Tyr, $^{125}$I-Tyr, mono-halo-Tyr, di-halo-Tyr, O-sulpho-Tyr, O-phospho-Tyr, and nitro-Tyr. Tyr residues may also be substituted with the 3-hydroxyl or 2-hydroxylisomers (meta-Tyr or ortho-Tyr, respectively) and corresponding O-sulpho- and O-phospho derivatives. Tyr residues can also be replaced with synthetic hydroxyl containing amino acids including, but not limited to 4-hydroxymethyl-Phe, 4-hydroxyphenyl-Gly, 2,6-dimethyl-Tyr and 5-amino-Tyr. Aliphatic amino acids may be substituted by synthetic derivatives bearing non-natural aliphatic branched or linear side chains $C_nH_{2n+2}$ up to and including n=8. Examples of suitable conservative substitutions by non-conventional amino acids are given in WO02/064740, the entire contents of which is incorporated herein by reference. According to the present invention substitutions in loop 1 are restricted to conservative substitutions.

Substitutions may also be "non-conservative", in which an amino acid residue which is present in a peptide is substituted with an amino acid having different properties, such as naturally-occurring amino acid from a different group (eg. substituting a charged or hydrophobic amino acid with alanine), or alternatively, in which a naturally-occurring amino acid is substituted with a non-conventional amino acid. According to the present invention such non-conservative substitutions are restricted to amino acid residues which are not part of loop 1 of the peptide, and that have little or no deleterious effect on activity. Amino acid substitutions are typically of single residues, but may be of multiple residues, either clustered or dispersed.

Additions encompass the addition of one or more naturally occurring or non-conventional amino acid residues. According to the present invention, except where an N-terminal residue is specified or where the complete sequence is designated, additions may occur at the N- or C-termini of the peptides according to the invention. Deletion encompasses the deletion of one or more amino acid residues. Many peptides according to the present invention represent derivatives of χ-MrIA which have undergone one or more amino acid deletions.

As stated above the present invention includes peptides in which one or more of the amino acids has undergone sidechain modifications. Examples of side chain modifications contemplated by the present invention include but are not limited to modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$; and N-acetylation.

The guanidine group of arginine residues may be modified by the formation of heterocyclic condensation products with reagents such as 2,3-butanedione, phenylglyoxal and glyoxal.

The tyrosine residue may be altered, for example by methoxylation at the 4-position. Tyrosine may also be altered by nitration with tetranitromethane to form a 3-nitrotyrosine derivative. Examples of tyrosine derivatives are given in WO02/064740.

The carboxyl group may be modified by carbodiimide activation via O-acylisourea formation followed by subsequent derivatisation, for example, to a corresponding amide.

Acidic amino acids may be substituted with tetrazolyl derivatives of Gly and Ala, as described in WO02/600923.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Any modification of cysteine residues must not affect the ability of the peptide to form the necessary disulphide bonds. It is also possible to replace the sulphydryl groups of cysteine with selenium equivalents such that the peptide forms a diselenium bond in place of one or more of the disulphide bonds, or mixed selenium/sulfide bonds. Individual Cys residues may also be replaced with homoCys or penicillamine so that disulfide bridges may be formed between Cys-homoCys, Cys-penicillamine or homoCys-penicillamine. Cys residues may also be replaced with isosteric lactam replacements as described in detail in WO02/600923.

Tryptophan residues may be modified by, for example, oxidation with N-bromosuccinimide or alkylation of the indole ring with 2-hydroxy-5-nitrobenzyl bromide or sulphenyl halides.

Modification of the imidazole ring of a histidine residue may be accomplished by alkylation with iodoacetic acid derivatives or N-carbethoxylation with diethylpyrocarbonate.

Proline residues may be modified by, for example, hydroxylation in the 4-position.

Other derivatives contemplated by the present invention include a range of glycosylation variants. Altered glycosylation patterns may result from expression of recombinant molecules in different host cells. Ser, Thr and Hyp residues may be modified to contain an O-glycan, while Asn and Gln residues can be modified to form a N-glycan. In accordance with the present invention, the term "glycan" refers to an N-, S- or O-linked mono-, di-, tri, poly- or oligosaccharide that can be attached to any hydroxy, amino or thiol group of natural of modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNac), D-fucose or D-arabinose. These saccharides may be structurally modified ie., with one or more O-sulphate, O-phosphate, O-acetyl or acidic groups such as sialic acid, including combinations thereof. The glycan may also include similar polyhydroxyl groups, such as D-penicillamine 2,5 and halogenated derivatives thereof or polypropylene glycol derivatives. The glycosidic linkage is beta and 1-4 or 1-3, preferably 1-3. The linkage between the glycan and the amino acid may be alpha or beta, preferably alpha and is 1-.

A list of some amino acids having modified side chains and other unnatural amino acids is shown in Table 1.

TABLE 1

| Non-conventional amino acid | Code |
| --- | --- |
| L-α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | DAla |
| D-arginine | DArg |
| D-asparagine | DAsn |
| D-aspartic acid | DAsp |
| D-cysteine | DCys |
| D-glutamine | DGln |
| D-glutamic acid | DGlu |
| D-histidine | DHis |
| D-isoleucine | DIle |
| D-leucine | DLeu |
| D-lysine | DLys |
| D-methionine | DMet |
| D-ornithine | DOrn |
| D-phenylalanine | DPhe |
| D-proline | DPro |
| D-serine | DSer |
| D-threonine | DThr |
| D-tryptophan | DTrp |
| D-tyrosine | DTyr |
| D-valine | DVal |
| D-α-methylalanine | DMala |
| D-α-methylarginine | DMarg |
| D-α-methylasparagine | nMasn |
| D-α-methylaspartate | DMasp |
| D-α-methylcysteine | DMcys |
| D-α-methylglutamine | DMgln |
| D-α-methylhistidine | DMhis |
| D-α-methylisoleucine | DMile |
| D-α-methylleucine | DMleu |
| D-αz-methyllysine | DMlys |
| D-α-methylmethionine | DMmet |
| D-α-methylornithine | DMorn |
| D-α-methylphenylalanine | DMphe |
| D-α-methylproline | DMpro |
| D-α-methylserine | DMser |
| D-α-methylthreonine | DMthr |
| D-α-methyltryptophan | DMtrp |
| D-α-methyltyrosine | DMty |
| D-α-methylvaline | DMval |
| D-N-methylalanine | DNmala |
| D-N-methylarginine | DNmarg |
| D-N-methylasparagine | DNmasn |
| D-N-methylaspartate | DNmasp |
| D-N-methylcysteine | DNmcys |
| D-N-methylglutamine | DNmgln |
| (-carboxyglutamate | Gla |
| 4-hydroxyproline | Hyp |
| 5-hydroxylysine | Hlys |
| 2-aminobenzoyl (anthraniloyl) | Abz |
| Cyclohexylalanine | Cha |
| Phenylglycine | Phg |
| 4-phenyl-phenylalanine | Bib |
| L-pyroglutamic acid | pGlu & Pyr |
| L-Citrulline | Cit |
| L-1,2,3,4-tetrahydroiso-quinoline-3-carboxylic acid | Tic |
| L-Pipecolic acid (homo proline) | Pip |
| L-homoleucine | Hle |
| L-Lysine (dimethyl) | DMK |
| L-Naphthylalanine | Nal |
| L-dimethyldopa or L-dimethoxyphenylalanine | DMD |
| L-thiazolidine-4-carboxylic acid | THZ |
| L-homotyrosine | hTyr |

TABLE 1-continued

| Non-conventional amino acid | Code |
| --- | --- |
| L-3-pyridylalanine | PYA |
| L-2-furylalanine | FLA |
| L-histidine(benzyloxymethyl) | HBO |
| L-histidine(3-methyl) | HME |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| N-cycloheptylglycine | Nchep |
| N-(3-guanidinopropyl)glycine | Narg |
| L-Diphenylalanine | DPA |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl) carbamylmethylglycine | Nnbhm |
| 1-carboxy-1-(2,2-diphenyl-ethylamino)cyclopropane | Nmbc |
| L-N-methylalanine | Nmala |
| L-N-methylarginine | Nmarg |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcyclopentylalanine | Mcpen |
| α-methyl-a-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(1-hydroxyethyl)glycine | Nthr |
| N-(hydroxyethyl)glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalani | Nmhphe |
| N-(N-(3,3-diphenylpropyl) carbamylmethylglycine | Nnbhe |
| O-methyl-L-serine | Omser |
| O-methyl-L-homoserine | Omhser |
| O-methyl-L-tyrosine | MeY |
| γ-aminobutyric acid | Gabu |
| O-methyl-L-homotyrosine | Omhtyr |
| L-β-homolysine | BHK |
| L-ornithine | Orn |
| N-cyclohexylglycine | Nchex |
| D-N-methylserine | Dnmser |

Particularly preferred sidechain modifications include the replacement of Tyr with MeY and/or replacement of Pro with Hyp and/or replacement of Leu with Hle or Nle.

These types of modifications, and others which involve more substantive sidechain modifications, may be important to stabilise the peptide if administered to an individual or used as a diagnostic reagent, or to improve solubility or bioavailability, or to provide other pharmacologies. For example it is possible to extend or contract sidechain length, or insert or remove functional groups to achieve these effects, eg by inserting nitroxide donor groups.

The peptides according to the present invention may be in the form of a salt, ester, amide, prodrug or, where appropriate, a cyclised derivative. The χ-conotoxins of the present invention are typically amidated at the C-terminal, however compounds with a free carboxyl terminus or other modifications, such as esterification at the C-terminal are considered to be within the scope of the present invention. Preferably the peptides are amidated or have a free carboxyl at the C-terminal. The peptides according to the present invention generally have a free N-terminus, although the N-terminus may be capped using a suitable capping group. Examples of suitable capping groups include, but are not limited to, acetyl (Ac), benzoyl (Ben) and Naphthyl (Nap).

Examples of suitable salts include the chloride, acetate, lactate and glutamate salts. Conventional procedures for the preparation of suitable salts are well known in the art.

The peptides according to the present invention may also be in the form of prodrugs. Prodrugs are understood to include all derivatives of peptides according to the invention which are readily convertible in vivo into the required active peptide. Conventional procedures for the preparation of suitable prodrugs according to the invention are described in text books, such as "Design of Prodrugs" ed. H. Bundgaard, Elsevier, 1985.

Certain peptides according to the present invention may also be in cyclised form, such that there is no N- or C-termini. Such peptide derivatives may have improved stability and bioavailability relative to the non-cyclised peptides. Methods for cyclising conotoxin peptides are described in WO 00/15654 (University of Queensland), the entire contents of which is incorporated herein by reference.

Certain peptides according to the present invention may also be in cyclised form, such that the N- or C-termini are linked head-to-tail either directly, or through the insertion of a linker moiety, such moiety itself generally consisting of one or more amino acid residues as required to join the backbone in such a manner as to avoid altering the three-dimensional structure of the peptide with respect to the noncyclised form. Such peptide derivatives may have improved stability and bioavailability relative to the non-cyclised peptides. Methods for cyclising conotoxin peptides are described in WO 00/15654 (University of Queensland), the entire contents of which is incorporated herein by reference.

Other procedures known in the art for selective oxidation of the cysteine residues may also be used such as those described in Tam J P, Lu Y A, Yang J L. "Marked increase in membranolytic selectivity of novel cyclic tachyplesins constrained with an antiparallel two-beta strand cystine knot framework", Biochem Biophys Res Commun. 2000; 267(3):783-790; Yu Q, Lehrer R I, Tam J P. "Engineered salt-insensitive α-defensins with end-to-end circularized structures" J Biol Chem. 2000; 275(6):3943-3949; and Tam J P, Lu Y A, Yang J L, Chiu K W. "An unusual structural motif of antimicrobial peptides containing end-to-end macrocycle and cystine-knot disulfides" Proc Natl Acad Sci USA. 1999; 96(16):8913-8918.

The peptides of the present invention retain the Cys residues and characteristic disulphide bonding pattern of χ-conotoxin peptides. Derivatives may include additional Cys residues provided they are protected during formation of the disulphide bonds.

In SEQ ID NOS. 3 and 4 the Gly residue in loop 1 may be conservatively substituted or subjected to conservative side chain modification. One non-limiting example of a modification is DLys.

In SEQ ID NOS. 3 and 4 the Tyr residue in loop 1 may be conservatively substituted or subjected to conservative side chain modification. Examples of suitable replacements or modifications include, but are not limited to, MeY and hTyr.

In SEQ ID NOS. 3 and 4 the Lys residue in loop 1 may be conservatively substituted or subjected to conservative side chain modification. Examples of suitable replacements or modifications include, but are not limited to, DMK. Other less favoured modifications include Ala, Leu, Arg, Phe, His, Nle and Cit.

In SEQ ID NOS. 3 and 4 the Leu residue in loop 1 may be conservatively substituted or subjected to conservative side chain modification. Examples of suitable replacements or modifications include, but are not limited to, Hle and Nle.

Chimeras of the χ-conotoxins of the present invention, with other conotoxins or additionally with other peptides or proteins, can be made to engineer the activity into other molecules, in some instances to produce a new molecule with extra functionality. For example, amino acids that bind to the N-type calcium channel can be combined with amino acids that inhibit NET to produce a peptide with activity at NET (using loop 1 residues of χ-conopeptides) and activity at the N-type calcium channel (using loop 2 of CVID), as in the N-/C-cylised CCSKLMYDCCGYKLG. Similarly, a cyclic peptide can be contrasted with loop 1 chi residues and a loop of amino acids having activity at opiate receptors, as in cCCRRQICCGYKLG. These chimeric peptides may be particularly useful as they possess pharmacologies that are additive or even synergistic, and are expected to be beneficial in the treatment of a wide range of pain syndromes that present in humans.

A subset of these MrIA analogues may act at receptors in addition to the NET allowing synergistic or additional effects. Preferably these additional interactions synergise to enhance the antinociceptive effects. More preferably, these additional interactions occur at opioid receptors, opioid receptor like receptors, GPCRs of the MRG family, the NMDA receptors, glutamate receptors, the neurokinins, cyclooxygenase receptors, serotergenic, receptors, adrenergic receptors, vanilloid receptors, benzodiazepines receptors, N-type calcium channel antagonists, neuronal nicotinic receptors, muscarinic acetylcholine capsaicin receptors, TNF-α, tetrodotoxin-resistant and tetrodotoxin-sensitive Na Channels, voltage-sensitive calcium channel and endothelian receptors.

Preferably the χ-conotoxin peptides according to the invention have 10 to 30 amino acids, more preferably 11 to 20.

The peptides according to the invention may be part of a larger peptide. For example, the N-terminus "head" region of the peptides of the first, second, third and seventh aspects of the present invention may be extended to any suitable length by introduction of additional amino acid residues. Similarly the C-terminus may also be extended by addition of a peptide "tail". In some cases the activity of the peptide can be improved by such modifications.

The peptides according to the present invention may be modified by biotinylation for use in biological assays, attachment of antibodies for targeting the site of action, attachment of sugars and lipids to improve permeability, and the like.

Examples of χ-conotoxin peptides according to the present invention include those listed in Table 2:

TABLE 2

| SEQ ID. NO. | Xaa1 | Xaa2 | Xaa3 | Xaa4 | Cys | Cys | Gly | Tyr | Lys | Leu | Cys | Xaa5 | Xaa6 | Cys | |
|---|---|---|---|---|---|---|---|---|---|---|---|---|---|---|---|
| 13 | | Tyr | Arg | Gly | Leu | Cys | Cys | Gly | MeY | Lys | Leu | Cys | Arg | Hyp | Cys |
| 14 | | Tyr | Arg | Gly | Nle | Cys | Cys | Gly | MeY | Lys | Leu | Cys | Arg | Hyp | Cys |
| 15 | Orn | Tyr | Arg | Gly | Nle | Cys | Cys | Gly | MeY | Lys | Leu | Cys | Arg | Hyp | Cys |
| 16 | | Trp | Arg | Gly | Leu | Cys | Cys | Gly | MeY | Lys | Leu | Cys | His | Hyp | Cys |
| 17 | | Orn | Arg | Gly | Nle | Cys | Cys | Gly | MeY | Lys | Leu | Cys | Arg | Hyp | Cys |
| 18 | Lys | Tyr | Arg | Gly | Nle | Cys | Cys | Gly | MeY | Lys | Leu | Cys | Arg | Hyp | Cys |
| 19 | | | BHK | Gly | Nle | Cys | Cys | Gly | MeY | Lys | Hle | Cys | His | Hyp | Cys |
| 20 | | Trp | Arg | Gly | Val | Cys | Cys | Gly | MeY | Lys | Leu | Cys | His | Hyp | Cys |
| 21 | | Trp | Lys | Gly | Val | Cys | Cys | Gly | MeY | Lys | Leu | Cys | His | Hyp | Cys |
| 22 | Phe | Arg | Tyr | Gly | Nle | Cys | Cys | Gly | MeY | Lys | Leu | Cys | Arg | Hyp | Cys |
| 23 | Tyr | Orn | Arg | Gly | Nle | Cys | Cys | Gly | MeY | Lys | Leu | Cys | Arg | Hyp | Cys |
| 24 | | DTrp | Arg | Gly | Leu | Cys | Cys | Gly | MeY | Lys | Leu | Cys | Arg | Ala | Cys |
| 25 | | Trp | Arg | Gly | Val | Cys | Cys | Gly | MeY | Lys | Leu | Cys | His | Hyp | Cys |
| 26 | | Trp | Arg | Gly | Leu | Cys | Cys | Gly | Tyr | Lys | Leu | Cys | His | Hyp | Cys |
| 27 | | | BHK | Gly | Nle | Cys | Cys | Gly | Tyr | Lys | Hle | Cys | His | Hyp | Cys |
| 28 | Tyr | Phe | Arg | Gly | Nle | Cys | Cys | Gly | MeY | Lys | Leu | Cys | Arg | Hyp | Cys |
| 29 | | Trp | Arg | Gly | Val | Cys | Cys | Gly | MeY | Lys | Leu | Cys | Arg | Ala | Cys |
| 30 | | Trp | Arg | Gly | Val | Cys | Cys | Gly | Tyr | Lys | Leu | Cys | His | Hyp | Cys |
| 31 | | | Trp | Gly | Leu | Cys | Cys | Gly | MeY | Lys | Leu | Cys | Arg | Tyr | Cys |
| 32 | | | BHK | Gly | Nle | Cys | Cys | Gly | MeY | Lys | Leu | Cys | His | Hyp | Cys |
| 33 | | Trp | Asn | Gly | Val | Cys | Cys | Gly | Tyr | Lys | Leu | Cys | Arg | Hyp | Cys |
| 34 | Ac | Tyr | Arg | Gly | Leu | Cys | Cys | Gly | MeY | Lys | Leu | Cys | Arg | Hyp | Cys |
| 35 | | | Trp | Gly | Leu | Cys | Cys | Gly | MeY | Lys | Leu | Cys | Arg | Hyp | Cys |
| 36 | | Trp | Arg | Gly | Leu | Cys | Cys | Gly | MeY | Lys | Leu | Cys | Arg | Lys | Cys |
| 37 | | Trp | Arg | Gly | Leu | Cys | Cys | Gly | MeY | Lys | Leu | Cys | Arg | Ala | Cys |
| 38 | | Trp | Arg | Gly | Val | Cys | Cys | Gly | Tyr | Lys | Leu | Cys | Arg | Ala | Cys |
| 39 | | Trp | Asn | Gly | Val | Cys | Cys | Gly | Tyr | Lys | Leu | Cys | Arg | Hyp | Cys |
| 40 | | Trp | Arg | Gly | Val | Cys | Cys | Gly | MeY | Lys | Leu | Cys | His | Ala | Cys |
| 41 | pGlu | Tyr | Arg | Gly | Nle | Cys | Cys | Gly | MeY | Lys | Leu | Cys | Arg | Hyp | Cys |
| 42 | | | Orn | Gly | Nle | Cys | Cys | Gly | MeY | Lys | Hle | Cys | His | Hyp | Cys |
| 43 | | Trp | Arg | Gly | Val | Cys | Cys | Gly | Tyr | Lys | Leu | Cys | His | Hyp | Cys | Tyr |
| 44 | | | Trp | Gly | Leu | Cys | Cys | Gly | MeY | Lys | Leu | Cys | Arg | Hyp | Cys | Tyr |
| 45 | | | Orn | Gly | Nle | Cys | Cys | Gly | MeY | Lys | Leu | Cys | His | Hyp | Cys |
| 46 | | Trp | Asn | Gly | Val | Cys | Cys | Gly | MeY | Lys | Leu | Cys | His | Hyp | Cys |
| 47 | | | Asn | Gly | Nle | Cys | Cys | Gly | MeY | Lys | Hle | Cys | His | Hyp | Cys |
| 48 | | | Orn | Gly | Nle | Cys | Cys | Gly | MeY | Lys | Nle | Cys | His | Hyp | Cys |
| 49 | | | BHK | Gly | Val | Cys | Cys | Gly | Tyr | Lys | Hle | Cys | His | Hyp | Cys |
| 50 | | Tyr | Asn | Gly | Nle | Cys | Cys | Gly | Tyr | Lys | Leu | Cys | His | Pro | Cys |

TABLE 2-continued

| SEQ ID. NO. | Xaa1 | Xaa2 | Xaa3 | Xaa4 | Cys | Cys | Gly | Tyr | Lys | Leu | Cys | Xaa5 | Xaa6 | Cys | |
|---|---|---|---|---|---|---|---|---|---|---|---|---|---|---|---|
| 51 | | Orn | Gly | Leu | Cys | Cys | Gly | MeY | Lys | Leu | Cys | His | Hyp | Cys | |
| 52 | | Orn | Gly | Nle | Cys | Cys | Gly | Tyr | Lys | Hle | Cys | His | Hyp | Cys | |
| 53 | | Trp | Asn | Gly | Val | Cys | Cys | Gly | MeY | Lys | Leu | Cys | His | Pro | Cys |
| 54 | | Trp | Arg | Gly | Val | Cys | Cys | Gly | Tyr | Lys | Leu | Cys | His | Ala | Cys |
| 55 | Asp | Tyr | Arg | Gly | Nle | Cys | Cys | Gly | MeY | Lys | Leu | Cys | Arg | Hyp | Cys |
| 56 | | Tyr | Asn | Gly | Val | Cys | Cys | Gly | Tyr | Lys | Hle | Cys | His | Pro | Cys |
| 57 | | | Asn | Gly | Nle | Cys | Cys | Gly | Tyr | Lys | Nle | Cys | His | Hyp | Cys |
| 58 | | | BHK | Gly | Nle | Cys | Cys | Gly | Tyr | Lys | Leu | Cys | His | Hyp | Cys |
| 59 | | | Asn | Gly | Val | Cys | Cys | Gly | Tyr | Lys | Leu | Cys | Trp | Pro | Cys |
| 60 | | Trp | Asn | Gly | Val | Cys | Cys | Gly | Tyr | Lys | Leu | Cys | Arg | Pro | Cys |
| 61 | | | Asn | Gly | Nle | Cys | Cys | Gly | MeY | Lys | Nle | Cys | His | Hyp | Cys |
| 62 | | Tyr | Asn | Gly | Val | Cys | Cys | Gly | MeY | Lys | Leu | Cys | Arg | Ala | Cys |
| 63 | | | Asn | Asp | Val | Cys | Cys | Gly | Tyr | Lys | Leu | Cys | His | Pro | Cys |
| 64 | | Trp | Arg | Gly | Leu | Cys | Cys | Gly | Tyr | Lys | Leu | Cys | Arg | Gly | Cys |
| 65 | | | pGlu | Gly | Leu | Cys | Cys | Gly | MeY | Lys | Leu | Cys | Arg | Hyp | Cys | Tyr |
| 66 | | | Orn | Gly | Nle | Cys | Cys | Gly | Tyr | Lys | Nle | Cys | His | Hyp | Cys |
| 67 | | hPhe | Asn | Gly | Val | Cys | Cys | Gly | Tyr | Lys | Leu | Cys | His | Hyp | Cys |
| 68 | | Tyr | Asn | Gly | Val | Cys | Cys | Gly | Tyr | Lys | Leu | Cys | Arg | Hyp | Cys |
| 69 | | Trp | Asn | Gly | Val | Cys | Cys | Gly | Tyr | Lys | Leu | Cys | Arg | Ala | Cys |
| 70 | Phe | Gly | Gly | Phe | Trp | Cys | Cys | Gly | MeY | Lys | Leu | Cys | Arg | Ala | Cys |
| 71 | | Tyr | Asn | Gly | Val | Cys | Cys | Gly | Tyr | Lys | Leu | Cys | Trp | Hyp | Cys |
| 72 | | Trp | Asn | Gly | Leu | Cys | Cys | Gly | Tyr | Lys | Leu | Cys | His | Hyp | Cys |
| 73 | | | BHK | Gly | Nle | Cys | Cys | Gly | Tyr | Lys | Leu | Cys | His | Pro | Cys |
| 74 | | | Asn | Gly | Nle | Cys | Cys | Gly | MeY | Lys | Leu | Cys | His | Hyp | Cys |
| 75 | | | BHK | Gly | Val | Cys | Cys | Gly | MeY | Lys | Leu | Cys | His | Pro | Cys |
| 76 | | | BHK | Gly | Val | Cys | Cys | Gly | Tyr | Lys | Hle | Cys | His | Pro | Cys |
| 77 | | | DArg | Gly | Val | Cys | Cys | Gly | MeY | Lys | Leu | Cys | His | Hyp | Cys |
| 78 | | Trp | Arg | Gly | Leu | Cys | Cys | Gly | Tyr | Lys | Leu | Cys | Arg | Ala | Cys |
| 79 | | | BHK | Gly | Val | Cys | Cys | Gly | MeY | Lys | Leu | Cys | His | Hyp | Cys |
| 80 | | | Asn | Gly | Nle | Cys | Cys | Gly | Tyr | Lys | Hle | Cys | His | Hyp | Cys |
| 81 | | Tyr | Asn | Gly | Val | Cys | Cys | Gly | Tyr | Lys | Leu | Cys | Arg | Ala | Cys |
| 82 | | Trp | Asn | Gly | Val | Cys | Cys | Gly | Tyr | Lys | Leu | Cys | His | Pro | Cys |
| 83 | | Phe | Gly | Gly | Phe | Cys | Cys | Gly | MeY | Lys | Leu | Cys | Arg | Ala | Cys |
| 84 | | Tyr | Asn | Gly | Val | Cys | Cys | Gly | Tyr | Lys | Leu | Cys | Arg | Pro | Cys |
| 85 | | Trp | Lys | Asp | Leu | Cys | Cys | Gly | Tyr | Lys | Leu | Cys | His | Pro | Cys |
| 86 | | Tyr | Asn | Gly | Val | Cys | Cys | Gly | MeY | Lys | Leu | Cys | His | Pro | Cys |
| 87 | | | BHK | Gly | Val | Cys | Cys | Gly | Tyr | Lys | Leu | Cys | Arg | Hyp | Cys |

TABLE 2-continued

| SEQ ID. NO. | | | | Xaa1 | Xaa2 | Xaa3 | Xaa4 | Cys Cys Gly Tyr Lys Leu Cys | Xaa5 | Xaa6 | Cys |
|---|---|---|---|---|---|---|---|---|---|---|---|
| 88 | | | | | Tyr | Asn | Gly | Val | Cys Cys Gly Tyr Lys Leu Cys | His | Hyp | Cys |
| 89 | | | | | Tyr | Asn | Gly | Val | Cys Cys Gly Tyr Lys Leu Cys | Arg | Pro | Cys |
| 90 | | | | | Trp | Lys | Asp | Leu | Cys Cys Gly Tyr Lys Leu Cys | Trp | Pro | Cys |
| 91 | | | | | Tyr | Asn | Gly | Val | Cys Cys Gly Tyr Lys Leu Cys | Trp | Pro | Cys |
| 92 | | | | | Trp | Lys | Asp | Val | Cys Cys Gly Tyr Lys Leu Cys | Trp | Pro | Cys |
| 93 | | | | | | BHK | Gly | Val | Cys Cys Gly Tyr Lys Leu Cys | His | Pro | Cys |
| 94 | | | | | Tyr | Asn | Gly | Val | Cys Cys Gly MeY Lys Leu Cys | — | Pro | Cys |
| 95 | | | | | Trp | BHK | Gly | Val | Cys Cys Gly Tyr Lys Leu Cys | His | Hyp | Cys |
| 96 | | | | | | Orn | Gly | Nle | Cys Cys Gly Tyr Lys Leu Cys | His | Hyp | Cys |
| 97 | | | | | | Asn | Gly | Leu | Cys Cys Gly Tyr Lys Leu Cys | His | Pro | Cys |
| 98 | | | | | | Arg | Gly | Val | Cys Cys Gly Tyr Lys Leu Cys | His | Pro | Cys |
| 99 | cyclic ( | | | Gly | Tyr | Lys | Leu | Gly | Cys Cys Gly Tyr Lys Leu Cys | — | — | Cys ) |
| 100 | | | Trp | Ala | Ala | Asn | Gly | Val | Cys Cys Gly Tyr Lys Leu Cys | His | Hyp | Cys |
| 101 | | | | | | BHK | Gly | Val | Cys Cys Gly Tyr Lys Leu Cys | His | Hyp | Cys |
| 102 | | | | | | Asn | Gly | Val | Cys Cys Gly Tyr Lys Leu Cys | His | Tic | Cys |
| 103 | | | | | | DArg | Gly | Val | Cys Cys Gly Tyr Lys Leu Cys | His | Hyp | Cys |
| 104 | | | | | | MeY | Asn | Gly | Val | Cys Cys Gly Tyr Lys Leu Cys | His | Pro | Cys |
| 105 | Gly | | Ile | Leu | Arg | Asn | Gly | Val | Cys Cys Gly Tyr Lys Leu Cys | His | Pro | Cys |
| 106 | | | | Trp | Ala | Asn | Gly | Val | Cys Cys Gly Tyr Lys Leu Cys | His | Hyp | Cys |
| 107 | | | | | | Nle | Gly | Val | Cys Cys Gly MeY Lys Leu Cys | His | Hyp | Cys |
| 108 | | | | | | Orn | Gly | Val | Cys Cys Gly Tyr Lys Leu Cys | His | Pro | Cys |
| 109 | | | Ac | Trp | BHK | Gly | Val | Cys Cys Gly Tyr Lys Leu Cys | His | Hyp | Cys |
| 110 | | | | | | Tyr | Asn | Lys | Val | Cys Cys Gly Tyr Lys Leu Cys | His | Pro | Cys |
| 111 | | | | | | BHK | Gly | Val | Cys Cys Gly Tyr Lys Leu Cys | His | Tic | Cys |
| 112 | | | | | | Asn | Gly | Nle | Cys Cys Gly Tyr Lys Leu Cys | His | Hyp | Cys |
| 113 | | | | | | Asn | Gly | Val | Cys Cys Gly MeY Lys Leu Cys | His | Pro | Cys |
| 114 | | | | | Ac | BHK | Gly | Val | Cys Cys Gly Tyr Lys Leu Cys | His | Hyp | Cys |
| 115 | | | | | | Asn | Gly | Leu | Cys Cys Gly Tyr Lys Leu Cys | His | Hyp | Cys |
| 116 | | | | | Tyr | Asn | Gly | Val | Cys Cys Gly Tyr Lys Leu Cys | His | Pro | Cys |
| 117 | | | | | | Asn | Gly | Val | Cys Cys Gly Tyr Lys Leu Cys | His | Lys | Cys |
| 118 | | | | | Tyr | Asn | Arg | Val | Cys Cys Gly Tyr Lys Leu Cys | His | Pro | Cys |
| 119 | | | | | | Nle | Gly | Val | Cys Cys Gly Tyr Lys Leu Cys | His | Hyp | Cys |
| 120 | | | | | Ben | Asn | Gly | Val | Cys Cys Gly Tyr Lys Leu Cys | His | Pro | Cys |
| 121 | | | | | | DLys | Gly | Val | Cys Cys Gly Tyr Lys Leu Cys | His | Hyp | Cys |
| 122 | | | | | | Asn | Lys | Val | Cys Cys Gly Tyr Lys Leu Cys | His | Pro | Cys |
| 123 | | | | | | Asn | Gly | Val | Cys Cys Gly MeY Lys Leu Cys | His | Hyp | Cys |
| 124 | | | | | | Asn | Ala | Val | Cys Cys Gly Tyr Lys Leu Cys | His | Hyp | Cys |
| 125 | | | | | | Asn | Gly | Ile | Cys Cys Gly Tyr Lys Leu Cys | His | Pro | Cys |

TABLE 2-continued

| SEQ ID. NO. | Xaa1 | Xaa2 | Xaa3 | Xaa4 | Cys | Cys | Gly | Tyr | Lys | Leu | Cys | Xaa5 | Xaa6 | Cys |
|---|---|---|---|---|---|---|---|---|---|---|---|---|---|---|
| 126 | | Asn | Gly | Val | Cys | Cys | Gly | Tyr | Lys | Nle | Cys | His | Hyp | Cys |
| 127 | | DMK | Gly | Val | Cys | Cys | Gly | Tyr | Lys | Leu | Cys | His | Hyp | Cys |
| 128 | | DAsn | Gly | Val | Cys | Cys | Gly | Tyr | Lys | Leu | Cys | His | Hyp | Cys |
| 129 | | Asn | Gly | Val | Cys | Cys | Gly | Tyr | Lys | Leu | Cys | His | Pip | Cys |
| 130 | | Ala | Gly | Val | Cys | Cys | Gly | Tyr | Lys | Leu | Cys | His | Hyp | Cys |
| 131 | Nap | Asn | Gly | Val | Cys | Cys | Gly | Tyr | Lys | Leu | Cys | His | Pro | Cys |
| 132 | Tyr | Asn | Nle | Val | Cys | Cys | Gly | Tyr | Lys | Leu | Cys | His | Pro | Cys |
| 133 | | Phe | Gly | Val | Cys | Cys | Gly | Tyr | Lys | Leu | Cys | His | Hyp | Cys |
| 134 | | Asn | Gly | Val | Cys | Cys | Gly | Tyr | Lys | Leu | Cys | Nal | Pro | Cys |
| 135 | | Thr | Gly | Val | Cys | Cys | Gly | Tyr | Lys | Leu | Cys | His | Hyp | Cys |
| 136 | | ABZ | Gly | Val | Cys | Cys | Gly | Tyr | Lys | Leu | Cys | His | Hyp | Cys |
| 137 | | Nap | Gly | Val | Cys | Cys | Gly | Tyr | Lys | Leu | Cys | His | Pro | Cys |
| 138 | | Asn | Gly | Thr | Cys | Cys | Gly | Tyr | Lys | Leu | Cys | His | Pro | Cys |
| 139 | | Cit | Gly | Val | Cys | Cys | Gly | Tyr | Lys | Leu | Cys | His | Hyp | Cys |
| 140 | pGlu | Asn | Gly | Val | Cys | Cys | Gly | MeY | Lys | Leu | Cys | His | Hyp | Cys |
| 141 | | Asn | Gly | Val | Cys | Cys | Gly | Tyr | Lys | Leu | Cys | His | MeY | Cys |
| 142 | | pGlu | Gly | Val | Cys | Cys | Gly | Tyr | Lys | Leu | Cys | His | Hyp | Cys |
| 143 | Ac | Asn | Gly | Val | Cys | Cys | Gly | Tyr | Lys | Leu | Cys | His | Hyp | Cys |
| 144 | | DpGlu | Gly | Val | Cys | Cys | Gly | Tyr | Lys | Leu | Cys | His | Hyp | Cys |
| 145 | | Asn | Gly | Val | Cys | Cys | Gly | Tyr | Lys | Leu | Cys | His | Ala | Cys |
| 146 | | Asn | Gly | Val | Cys | Cys | Gly | Tyr | Lys | Leu | Cys | His | Pro | Cys |
| 147 | | Asp | Gly | Val | Cys | Cys | Gly | Tyr | Lys | Leu | Cys | His | Hyp | Cys |
| 148 | | | | Val | Cys | Cys | Gly | Tyr | Lys | Leu | Cys | — | — | Cys |
| 149 | | Asn | Gly | Val | Cys | Cys | Gly | Tyr | Lys | Leu | Cys | His | DMD | Cys |
| 150 | | Asn | Gly | Ala | Cys | Cys | Gly | Tyr | Lys | Leu | Cys | His | Hyp | Cys |
| 151 | | Asp | Gly | Val | Cys | Cys | Gly | Tyr | Lys | Leu | Cys | His | Pro | Cys |
| 152 | Ac | Asn | Gly | Val | Cys | Cys | Gly | Tyr | Lys | Leu | Cys | His | Pro | Cys |
| 153 | | Asn | Gly | Ala | Cys | Cys | Gly | Tyr | Lys | Leu | Cys | His | Hyp | Cys |
| 154 | | pGlu | Asp | Val | Cys | Cys | Gly | Tyr | Lys | Leu | Cys | His | Hyp | Cys |
| 155 | | Asn | Gly | Val | Cys | Cys | Gly | Tyr | Lys | Leu | Cys | His | Phe | Cys |
| 156 | | Asn | Ser | Val | Cys | Cys | Gly | Tyr | Lys | Leu | Cys | His | Pro | Cys |
| 157 | pGlu | Asn | Gly | Val | Cys | Cys | Gly | Tyr | Lys | Leu | Cys | His | Hyp | Cys |
| 158 | | Asn | Gly | Val | Cys | Cys | Gly | Tyr | Lys | Leu | Cys | His | THZ | Cys |
| 159 | | Asn | Gly | Val | Cys | Cys | Gly | Tyr | Lys | Leu | Cys | His | Glu | Cys |
| 160 | | Asn | Gly | Abu | Cys | Cys | Gly | Tyr | Lys | Leu | Cys | His | Hyp | Cys |
| 161 | Ac | Tyr | Asn | Gly | Val | Cys | Cys | Gly | Tyr | Lys | Leu | Cys | His | Pro | Cys |
| 162 | | Asn | Gly | Val | Cys | Cys | Gly | Tyr | Lys | Leu | Cys | His | Nle | Cys |

TABLE 2-continued

| SEQ ID. NO. | Xaa1 | Xaa2 | Xaa3 | Xaa4 | Cys Cys Gly Tyr Lys Leu Cys | Xaa5 | Xaa6 | Cys | |
|---|---|---|---|---|---|---|---|---|---|
| 163 | Tyr | Asn | Gly | Val | Cys Cys Gly Tyr Lys Leu Cys | Gln | Pro | Cys | |
| 164 | | DpGlu | Gly | Val | Cys Cys Gly Tyr Lys Leu Cys | His | Hyp | Cys | OH |
| 165 | | Asn | Gly | Val | Cys Cys Gly Tyr Lys Leu Cys | His | Tyr | Cys | |

These peptides can also be labelled and used to establish binding assays to identify new molecules that act at the same site. For example, a labelled peptide ligand could have tritium included or may have radio-active iodine or similar attached through a Tyr or other appropriate residue. A Tyr scan through each peptide will establish a suitable location for incorporation of the Tyr. The inhibition of binding of such labelled peptides to tissue homogenates or expressed transporters by compounds or mixtures would permit identification of new peptides active at this site, including peptides present in serum and nerve and muscle tissue of mammals, including human tissues. The assay will also allow identification of non-peptide molecules that also act at the same site as χ-conotoxin peptides, and that may have utility as orally active forms of these peptides. Labelled peptides will additionally permit autoradiographic studies to identify the location of the peptide binding across various tissues.

Contrary to what was proposed in WO00/20444 the χ-conotoxin peptides have been found to be non-competitive inhibitors in relation to noradrenaline, but competitive in relation to small molecules that also bind to the noradrenaline transporter, such as mazindol, cocaine and tricyclic antidepressants, such as desipramine.

Accordingly binding assays using labelled peptides of the present invention, preferably radio isotopically labelled, can be used to discover small molecules that could act as non-competitive inhibitors of the noradrenaline transport through the noradrenaline transporter. Preferably this assay would be conducted in the presence of blocking concentrations of noradrenaline or related small molecules which do not overlap with the chi conopeptide binding site but which overlap with many small molecule inhibitors of the noradrenaline transporter (e.g. tricyclic antidepressants).

The χ-conotoxins of the present invention may be prepared using standard peptide synthetic methods followed by oxidative disulfide bond formation. For example, the linear peptides may be synthesised by solid phase methodology using BOC chemistry, as described by Schnoltzer et al (1992). Following deprotection and cleavage from the solid support the reduced peptides are purified using preparative chromatography. The purified reduced peptides are oxidised in buffered systems, for example as described in example 2. The oxidised peptides were purified using preparative chromatography.

References describing the synthesis of conotoxins include Sato et al, Lew et al and WO 91/07980.

Some of the χ-conotoxins according to the present invention may also be prepared using recombinant DNA technology. A nucleotide sequence encoding the desired peptide sequence, or its precursor, may be inserted into a suitable vector and protein expressed in an appropriate expression system. In some instances, further chemical modification of the expressed peptide may be appropriate, for example C-terminal amidation or post translational modification of particular residues. Under some circumstances it may be desirable to undertake oxidative bond formation of the expressed peptide as a chemical step following peptide expression. This may be preceded by a reductive step to provide the unfolded peptide. Those skilled in the art may readily determine appropriate conditions for the reduction and oxidation of the peptide.

The invention further provides an isolated nucleic acid molecule comprising a sequence of nucleotides encoding or complementary to sequence encoding a χ-conotoxin peptide as described above.

It may also be possible to prepare antiidiotypic antibodies using techniques known to the art. These antiidiotypic antibodies and their use as therapeutic agents represent a further aspect of the present invention.

The nucleic acid molecules of the present invention may be in isolated form or they may be integrated into or ligated to or otherwise fused or associated with other genetic molecules such as vector molecules and in particular expression vector molecules. Vectors and expression vectors are generally capable of replication and, if applicable, expression in one or both of a prokaryotic cell or a eukaryotic cell. Preferably, prokaryotic cells include *E. coli, Bacillus* sp and *Pseudomonas* sp. Preferred eukaryotic cells include yeast, fungal, mammalian and insect cells.

Accordingly, another aspect of the present invention contemplates a genetic construct comprising a vector portion and a gene capable of encoding a peptide according to the invention, or a peptide which can be post translationally modified to provide a peptide according to the invention.

Preferably, the gene portion of the genetic construct is operably linked to a promoter on the vector such that said promoter is capable of directing expression of the gene portion in an appropriate cell.

The present invention extends to such genetic constructs and to prokaryotic or eukaryotic cells comprising same.

It should thus be understood that the terms conotoxin peptide or conotoxins are not limited to naturally occurring toxic peptides obtained from the genus *Conus* but rather simply indicates an initial source from which the peptides have been derived. Conotoxin peptides are may be synthetically created, non-naturally occurring non-toxic peptide derivatives. Conopeptides is an alternative term interchangeable with conotoxin peptides.

The χ-conotoxin peptides according to the present invention are active in inhibiting neuronal noradrenaline transporter. Accordingly the invention provides the use of the χ-conotoxin peptides as inhibitors of neuronal noradrenaline transporter, and in the treatment or prophylaxis of diseases or conditions in relation to which the inhibition of neuronal noradrenaline transporter is associated with effective treatment. Such activity in pharmacological agents is associated with activity in the prophylaxis or treatment of diseases or conditions of the urinary or cardiovascular systems, or mood disorders, or in the treatment or control of acute, chronic and or neuropathic pain, migraine or inflammation.

Examples of the formulation and use of noradrenaline reuptake inhibitors in therapy can be found in Ardid, D et al., (1992) Fund. Clinical Pharmacology 6(2): 75-8; Yaksh, T. L. (1985) Pharmacology Biochemistry and Behaviour 22:845-858; Yaksh, T. L. & Takano, Y. (1992) J. Pharmacology & Experimental Therapeutics 261(2): 764-772; Yaksh, T. L. & Howe, J. R. (1982) J. Pharmacology & Experimental Therapeutics 220(2): 311-321; Howe, J. R. et al., (1983) J. Pharmacology & Experimental Therapeutics 224(3): 552-558; Solomon et al., (1989) J. Pharmacology & Experimental Therapeutics 251(1): 28-38; Fleetwood-Walker, S. M. et al., (1985) Brain Research 334:243-254; Takagi, H & Harima, A. (1996) European Neuropsychopharmacology 6, 43-47; Eisenach, J. C. et al (1998) Anesth Analg 87, 591-6; Dubner, R. & Hargreaves, K M (1989) Clin J Pain, 5 pS1-6; Max, M B (1992) N Engl J Med 326, p 1287-8; Atkinson, J H et al (1998) Pain 76, p 287-96; Mico, J. A. et al., (1997) European Neuropsychopharmacology 7, S162.

Accordingly the present invention provides a method for the treatment or prophylaxis of urinary or cardiovascular conditions or diseases or mood disorders or for the treatment or control of pain or inflammation including the step of administering to a mammal an effective amount of an isolated, synthetic or recombinant χ-conotoxin peptide having the ability to inhibit neuronal noradrenaline transporter, wherein said χ-conotoxin peptide comprises the following sequence of amino acids:

```
                                      SEQ ID NO. 3
    Cys Cys Gly Tyr Lys Leu Cys Xaa5 Xaa6 Cys
``` where Xaa5 and Xaa6 are independently absent or represent any amino acid residue except Cys, or such a sequence in which Gly, Tyr, Lys or Leu are subject to conservative amino acid substitution or side chain modification, with the proviso that the peptide is not χ-MrIA or χ-MrIB; or a salt, ester, amide, prodrug or cyclised derivative thereof.

According to this embodiment of the invention the peptide may be a peptide of SEQ ID NO. 4, 5 or 6 as described above.

In performing the method according to the present invention the administration of the χ-peptide may be performed in conjunction with other therapies useful in the treatment of the condition, disease or disorder. Accordingly the peptide may be administered substantially simultaneously or sequentially with other agents useful in the treatment of the conditions, diseases or disorders. Where the co-administration is simultaneous, the peptide may be formulated in a composition with one or more of the other agents. The co-administration of other agents can be performed via the same or different route to the route of administration for the χ-peptide. Where the method is for the treatment or control of acute, chronic and/or neuropathic pain or migraine, the peptide may be administered substantially simultaneously or sequentially with an analgesic agent selected from the group consisting of opioid analgesics, opioid receptor-like antagonists, GPCR antagonists of the MRG family, NMDA antagonists, substance P antagonists, COX 1 and COX 2 inhibitors, tricyclic antidepressants (TAC), selective serotonin reuptake inhibitors (SSRI), capsaicin receptor antagonists, anaesthetic agents, benzodiazepines, skeletal muscle relaxants, migraine therapeutic agents, anti-convulsants, anti-hypertensives, anti-arrhythmics, antihistamines, steroids, caffeine, N-type calcium channel antagonists, nicotinic receptor partial agonists and antagonists, vanilloid receptor antagonists and agonists, TNF-∀ antagonists and antibodies, inhibitors of tetrodotoxin-sensitive Na Channels, P-type channel inhibitors, endothelian antagonists and botulinum toxin. The peptide may also be administered simultaneously with two or more other agents, for example mixtures of SSRIs and noradrenaline reuptake inhibitors.

Where the analgesic agent is an opioid receptor-like analgesic agent it is preferably selected from naltrexone and nalmefene; their pharmaceutically active salts and their optical isomers.

Where the analgesic agent is an opioid analgesic agent it is preferably selected from propoxyphene, meperidine, hydromorphone, hydrocodone, morphine, codeine and tramodol; their pharmaceutically active salts and their optical isomers.

Where the analgesic agent is an NMDA antagonist analgesic agent it is preferably selected from 2-piperdino-1alkanol derivatives, dextromethorphan, eliprodil, and ifenprodil; their pharmaceutically active salts and their optical isomers.

Where the analgesic agent is a P antagonist analgesic agent it is preferably selected from 2-phenyl-piperidin-3-yl or 2-diphenylmethyl-1-azabicyclo[2.2.2]-octane-3-amine derivatives as described in U.S. Patent Application No. 2001/00336943 A1 (Coe et al.); their pharmaceutically active salts and their optical isomers.

Where the analgesic agent is a COX 2 inhibition analgesic agent it is preferably selected from rofecoxib and celecoxib; their pharmaceutically active salts and their optical isomers.

Where the analgesic agent is an anaesthetic analgesic agent it is preferably selected from nitrous oxide, halothane, lidocaine, etidocaine, ropivacaine, chloroprocaine, sarapin and bupivacaine; their pharmaceutically active salts and their optical isomers.

Where the analgesic agent is a benzodiazepine analgesic agent it is preferably selected from diazepam, chlordiazepoxide, alprazolam, lorazepam, midazolam, L-365260; their pharmaceutically active salts and their optical isomers.

Where the analgesic agent is a skeletal muscle relaxant analgesic agent it is preferably selected from flexeril, carisoprodol, robaxisal, norgesic and dantrium their pharmaceutically active salts and their optical isomers.

Where the analgesic agent is a migraine therapeutic agent it is preferably selected from elitriptan, sumatriptan, rizatriptan, zolmitriptan, and naratriptan their pharmaceutically active salts and their optical isomers.

Where the analgesic agent is an anticonvulsant analgesic agent it is preferably selected from gabapentin, pregabalin, carbamazepine, and topiramate and valproic acid their pharmaceutically active salts and their optical isomers.

Where the analgesic agent is a COX 1 inhibitor analgesic agent it is preferably selected from salycylic acid, acetominophen, diclofenac, piroxican indomethacin, ibuprofen, and naproxen their pharmaceutically active salts and their optical isomers.

Where the analgesic agent is a tricyclic antidepressant analgesic agent it is preferably selected from amitriptyline, desipramine, perphenazine, protriptyline, and tranylcypromine their pharmaceutically active salts and their optical isomers.

Where the analgesic agent is a SSRI analgesic agent it is preferably selected from tramadol and milnacipran; their pharmaceutically active salts and their optical isomers.

Where the analgesic agent is a mixture of SSRI and Noradrenaline reuptake inhibitors, the latter is preferably selected from reboxetine and atomoxetine; their pharmaceutically active salts and their optical isomers.

The analgesic agent may also be selected from adenosine, baclofen, clonidine, mexilitene, diphenyl-hydramine, hydroxysine, caffeine, prednisone, methylprednisone, decadron, paroxetine, sertraline, fluoxetine, Ziconotide® and levodopa their pharmaceutically active salts and their optical isomers.

Where the analgesic agent is a TNF-α antagonist or antibody, the agent is preferably selected from etanercept, infliximab and thalidomide; their pharmaceutically active salts and their optical isomers.

Where the analgesic agent is an endothelian antagonist, the agent is preferably selected from bosentan and tesosentan; their pharmaceutically active salts and their optical isomers.

Where the analgesic agent is a vanilloid antagonist, the analgesic agent is preferably selected from ananamide, capsazepine, thiocarbamic acid derivatives (as described in WO02/16317 A1) and thiourea derivatives (as described in WO02/16318 A1); their pharmaceutically active salts and their optical isomers.

Where the analgesic agent is selected from nicotine receptor partial agonist it is preferably selected from 1,2,3,4,5,6-hexahydro-1,5-methano-pyrido[1,2-a][1,5]diazocin-8-one derivatives, diazatetracyclo[9.3.1.0.sup.2,10.0.sup.4,8]pentadeca-2(10),3,8-triene derivatives, 10-aza-tricyclo[6.3.1.0.sup.2,7]dodeca-2(7),3,5-triene derivatives, triazatetracyclo[9.3.1.0.sup.2,10.0.sup.4,8]pentadeca-2(10),3,5,8-tetraene derivatives, 5,8,14-triazatetracyclo[10.3.1.0.sup.2,11.0.sup.4,9]hexadeca-2(11),3,5,7,9-pentaene derivatives, diazatetracyclo[9.3.1.0.sup.2,10.0.sup.4,8]pentadeca-2(10),3,6,8-tetraene derivatives, 10-azatricyclo[6.3.1.0.sup.2,7]dodeca-2(7),3,5-triene derivatives, 5,7,14-triazatetracyclo[10.3.1.0.sup.2,10.0.sup.4,8]hexadeca-2(10),3,5,8-tetraene derivatives, 5,8,15-triazatetracyclo[11.3.1.0.sup.2,11.0.sup.4,9]heptadeca-2(11),3,5,7,9-pentaene derivatives, 5,14-diazatetracyclo[10.3.1.0.sup.2,10.0.sup.4,8]hexadeca-2(10),3,5,8-tetraene derivatives, 11-azatricyclo[7.3.1.0.sup.2,7]trideca-2(7),3,5-triene derivatives, all of which are described in U.S. Patent Application No. 2001/00336943 A1 and their pharmaceutically acceptable salts and their optical isomers.

Examples of conditions associated with acute, chronic and/or neuropathic pain and inflammatory pain include soft tissue and peripheral damage, such as acute trauma, osteoarthritis, rheumatoid arthritis, musculo-skeletal pain, particularly after trauma, spinal pain, dental pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhea, and labour pain; pain associated with nerve and root damage, such as pain associated with peripheral nerve disorders, for example, nerve entrapment and brachial plexus avulsions, amputation, peripheral neuropathies, neuralgia, tic douloureux, atypical facial pain, nerve root damage, pain and/or chronic nerve compression, and arachnoiditis; pain associated with carcinoma, often referred to as cancer pain; pain associated with AIDS, central nervous system pain, such as pain due to spinal cord or brain stem damage; low back pain; sciatica; headache, including migraine, acute or chronic tension headache, cluster headache, temporomandibular pain and maxillary sinus pain; ankylosing spondylitis, gout; post operative pain; phantom pains; diabetic neuropathy; shingles; and scar pain.

Examples of the formulation and use of conotoxin peptides in the treatment of pain can be found in WO9107980; U.S. Pat. No. 5,587,454 and WO9701351. These documents relate to omega conotoxins. Also see Bowersox S S, Gadbois T, Singh T, Pettus M, Wang Y X & Luther R R (1996) J Pharmacol Exp Ther, 279(3) pages 1243-9 which relates to conotoxin peptides that are selective N-type Voltage-sensitive calcium channel blockers and their use in the treatment of acute, persistent and neuropathic pain in rats.

Examples of diseases or conditions of the urinary system include urinary and fecal incontinence. Examples of cardiovascular diseases or conditions include arrhythmias of various origins and coronary heart failure. Examples of mood disorders include depression, anxiety, cravings, an addictive disorder and withdrawal syndrome, an adjustment disorder, age-associated learning and mental disorders, anorexia nervosa, apathy, attention-deficit disorders due to general medical conditions, attention-deficit hyperactivity disorder, bipolar disorder, bulimia nervosa, chronic fatigue syndrome, chronic or acute stress, conduct disorder, cyclothymic disorder, depression, dysthymic disorder, fibromyalgia and other somatoform disorders, generalised anxiety disorder, incontinence, inhalation disorders, intoxication disorders, mania, obesity, obsessive compulsive disorders and related spectrum disorders, oppositional defiant disorder, panic disorder, peripheral neuropathy, post-traumatic stress disorder, premenstrual dysphoric disorder, psychotic disorders, seasonal affective disorder, sleep disorders, social phobia, specific developmental disorders, selective serotonin reuptake inhibition (SSRI) "poop out" syndrome, and TIC disorders.

Examples of the use of selective noreprinephrine reuptake inhibitors in the treatment of diseases or conditions of the urinary system include Springer, J P., Kropp, B P & Thor K B (1994) J Urol 152(2), p 515-9 (relates to lower urinary tract); Penttila, O. et al (1975) Ann Clin Res (7), 32-6 (relates to treatment of ulcerative colitis) and Dinan, T G et al (1990) J Psychosom Res 34, p 575-80 (relates to treatment of irritable bowel syndrome).

Preferably the mammal is in need of such treatment although the peptide may be administered in a prophylactic sense.

The invention also provides a composition comprising an isolated, synthetic or recombinant χ-conotoxin peptide having the ability to inhibit neuronal noradrenaline transporter, wherein said χ-conotoxin peptide comprises the following sequence of amino acids:

SEQ ID NO. 3
Cys Cys Gly Tyr Lys Leu Cys Xaa5 Xaa6 Cys where Xaa5 and Xaa6 are independently absent or represent any amino acid residue except Cys, or such a sequence in which loop 1 residues Gly, Tyr, Lys or Leu are subject to conservative amino acid substitution or side chain modification, with the proviso that the peptide is not χ-MrIA or χ-MrIB; or a salt, ester, amide, prodrug or cyclised derivative thereof, and a pharmaceutically acceptable carrier or diluent.

According to this embodiment of the invention the peptide may be a peptide of SEQ ID NO. 4, 5 or 6 as described above.

Preferably the composition is in the form of a pharmaceutical composition.

There is also provided the use of an isolated, synthetic or recombinant χ-conotoxin peptide having the ability to inhibit neuronal noradrenaline transporter, wherein said α-conotoxin peptide comprises the following sequence of amino acids:

SEQ ID NO. 3
Cys Cys Gly Tyr Lys Leu Cys Xaa5 Xaa6 Cys where Xaa5 and Xaa6 are independently absent or represent any amino acid residue except Cys, or such a sequence in which loop 1 residues Gly, Tyr, Lys or Leu are subject to conservative amino acid substitution or side chain modification, with the proviso that the peptide is not χ-MrIA or χ-MrIB; or a salt, ester, amide, prodrug or cyclised derivative thereof, in the manufacture of a medicament for the treatment or prophylaxis of urinary or cardiovascular conditions or diseases, or mood disorders, or for the treatment or control of pain or inflammation.

According to this embodiment of the invention the peptide may be a peptide of SEQ ID NO. 4, 5 or 6 as described above.

It is also noted that noradrenaline transporter is expressed not only by nerve cells, but also by other tissues including the placenta, pulmonary endothelial cells and the uterus. The peptides according to the present invention may also be effective in inhibiting these noradrenaline transporters, and may be useful in treating conditions in which these transporters are implicated.

As will be readily appreciated by those skilled in the art, the route of administration and the nature of the pharmaceutically acceptable carrier will depend on the nature of the condition and the mammal to be treated. It is believed that the choice of a particular carrier or delivery system, and route of administration could be readily determined by a person skilled in the art. In the preparation of any formulation containing the peptide actives care should be taken to ensure that the activity of the peptide is not destroyed in the process and that the peptide is able to reach its site of action without being destroyed. In some circumstances it may be necessary to protect the peptide by means known in the art, such as, for example, micro encapsulation. Similarly the route of administration chosen should be such that the peptide reaches its site of action.

For example the preferred route of administration for the treatment of urinary diseases is oral, topical, intranasal, intrarectal, intramucosal and intravenous. The same may be used for the treatment of pain and mode disorders, in addition to intrathecal administration. A method and formulations for use with conotoxin peptides in intrathecal administration is described in WO 9701351, the contents of which are incorporated by cross-reference.

The pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

Those skilled in the art may readily determine appropriate formulations for the peptides or modified peptides of the present invention using conventional approaches. Identification of preferred pH ranges and suitable excipients, for example antioxidants, is routine in the art (see for example Cleland et al, 1993). Buffer systems are routinely used to provide pH values of a desired range and include carboxylic acid buffers for example acetate, citrate, lactate and succinate. A variety of antioxidants are available for such formulations including phenolic compounds such as BHT or vitamin E, reducing agents such as methionine or sulphite, and metal chelators such as EDTA.

Conventional approaches for the formulation of pharmaceutically active peptides are described in the following articles, the methodology of which are incorporated by reference: Ryan, J et al., (1986) Clin Pharmacol Ther (39), 40-2. (a clinical trial detailing the oral administration of the peptide nifalatide); Krames E. S. et al. (1986) Pain 24, 205-9 (describes the intrathecal delivery of a peptide); WO9614079A1 (which describes oral and rectal administration of formulations of the peptide cyclosporin); WO9640064A1 (which describes formulations for peptide stability); WO9805309A1 (describes peptide formulations—a pharmaceutical composition of cyclosporin for internal use and WO9802148A2 (which describes sustained release rectal and oral peptide formulations).

The solvent or dispersion medium for the injectable solution or dispersion may contain any of the conventional solvent or carrier systems for peptide actives, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolality, for example, sugars or sodium chloride. Preferably, the formulation for injection will be isotonic with blood. Prolonged absorption of the injectable compositions can be brought about by the use in the compositions of agents delaying absorption, for example, aluminum monostearate and gelatin. Pharmaceutical forms suitable for injectable use may be delivered by any appropriate route including intravenous, intramuscular, intracerebral, intrathecal, epidural injection or infusion.

Sterile injectable solutions are prepared by incorporating the active compounds in the required amount in the appropriate solvent with various of the other ingredients such as these enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying a of a previously sterile-filtered solution of the active ingredient plus any additional desired ingredients.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations preferably contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to any other forms suitable for administration, for example topical application such as creams, lotions, transdermal patches, sprays and gels, or compositions suitable for inhalation or intranasal delivery, for example solutions or dry powders.

Parenteral dosage forms are preferred, including those suitable for intravenous, subcutaneous, intrathecal, intracerebral or epidural delivery.

The composition may also be formulated for delivery via slow release implants, including implantable pumps, such as osmotic pumps.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form. A unit dosage form can, for example, contain the principal active compound in amounts ranging from 0.25 µg to about 2000 mg. Expressed in proportions, the active compound is generally present in from about 0.25 µg to about 200 mg/ml of carrier. In the case of compositions containing supplementary active ingredients, the dosages are determined by reference to the usual dose and manner of administration of the said ingredients.

The invention will now be described with reference to the accompanying drawings and examples, however it is to be understood that the particularity of the following description is not to supersede the generality of the preceding description of the invention.

Referring to the Figure:

FIG. 1: Anti-allodynic effects of (A) i.t. SEQ ID NO. 20 and (B) MrIA in Chronic Constriction Injury (CCI) of the rat sciatic nerve.

EXAMPLES

Example 1

Synthesis a) Assembly

The peptides described herein were prepared according to the following methods:

(i) Assembly of MrIA and some MrIA derivatives was carried out using Fmoc-chemistry methods adapted from that described by Schnolzer et al., (1992) on a Polymer Labs Rink amide resin. Conventional Trt/t-Bu side chain protection was used throughout. The coupling efficiency was monitored using the ninhydrin test (Sarin et al., 1981) until a coupling efficiency of 99.5% or better was achieved. In some cases a second coupling step was required to achieve this level of coupling efficiency.

Cleavage was carried out using a mixture of TFA:water: triisopropylsilane:EDT (90:5:2.2:2.5) over 5 h at room temperature, then the product obtained by precipitation from cold diethyl ether. Purification of the crude reduced product was carried out by RP-HPLC on a Vydac C-8 column using a 1%/min gradient from 0% B to 45% B where A=0.1% TFA/water, B=90% Acetonitrile/water plus 0.043% TFA. Eluent was delivered to a mass spectrometer and samples collected on the basis of mass directed fractionation (MDF).

(ii) Other MrIA derivatives were prepared using Boc-chemistry and conventional side chain protecting groups on a MBHA resin using (Schnolzer et al, 1992). Cleavage is carried out using HF: scavengers (9:1) for 1 h at 0 to −10EC.

b) Oxidation

Oxidation of the pure reduced peptides was carried out using the following optimised buffer systems:

(i) 30% DMSO/0.1M $NH_4HCO_3$ at pH 6 for 12 h purified by RP-HPLC on a C-8 column as above;
(ii) 30% isopropanol/0.1M $NH_4HCO_3$ at pH 8.0; and
(iii) Mixture of isopropanol/DMSO/0.1M $NH_4HCO_3$ pH 8.0.

In each case the desired product was purified by RP-HPLC on a C-8 column as above.

c) In Addition to Preparing Peptides According to the Invention, the Peptides Listed in Table 3 were Also Prepared:

TABLE 3

| SEQ ID NO. | Xaa1 | Xaa2 | Xaa3 | Xaa4 | Cys | Cys | Gly | Tyr | Lys | Leu | Cys | Xaa5 | Xaa6 | Cys | |
|---|---|---|---|---|---|---|---|---|---|---|---|---|---|---|---|
| 166 | | Asn | Gly | Val | Cys | Cys | DLys | Tyr | Lys | Leu | Cys | His | Pro | Cys | |
| 167 | | Asn | Gly | Val | Cys | Cys | Gly | Tyr | DMK | Leu | Cys | His | Hyp | Cys | |
| 168 | | Asn | Gly | Val | Cys | Cys | Gly | hTyr | Lys | Leu | Cys | His | Hyp | Cys | |
| 169 | | Asn | Gly | Val | Cys | Cys | Gly | Tyr | Lys | Leu | Cys | PYA | Pro | Cys | |
| 170 | Tyr | Asn | Gly | Val | Cys | Cys | Gly | Tyr | Lys | Leu | Cys | Lys | Pro | Cys | |
| 171 | Tyr | Asn | Gly | Val | Cys | Cys | Gly | Leu | Lys | Leu | Cys | His | Pro | Cys | |
| 172 | | Asn | Gly | Val | Cys | Cys | Gly | Tyr | Ala | Leu | Cys | His | Pro | Cys | |
| 173 | | | | | Cys | Cys | Gly | Tyr | Lys | Leu | Cys | His | Hyp | Cys | |
| 174 | Tyr | Asn | Gly | Val | Cys | Cys | Gly | Tyr | Leu | Leu | Cys | His | Pro | Cys | |
| 175 | Tyr | Asn | Gly | Val | Cys | Cys | Gly | Tyr | Lys | Asn | Cys | His | Pro | Cys | |
| 176 | | Asn | Gly | Val | Cys | Cys | Gly | FLA | Lys | Leu | Cys | His | Pro | Cys | |
| 177 | | Asn | Gly | Val | Cys | Cys | Gly | Tyr | Arg | Leu | Cys | His | Hyp | Cys | |
| 178 | | Asn | Gly | Val | Cys | Cys | Gly | Tyr | Lys | Leu | Cys | HBO | Pro | Cys | |
| 179 | Tyr | Asn | Gly | Val | Cys | Cys | Gly | Tyr | Phe | Leu | Cys | His | Pro | Cys | |
| 180 | | Asn | Gly | Val | Cys | Cys | Gly | Tyr | Lys | Leu | Cys | HME | Pro | Cys | |
| 181 | | Asn | Gly | Val | Cys | Cys | Gly | Tyr | His | Leu | Cys | His | Pro | Cys | |
| 182 | | pGlu | Gly | Val | Cys | Cys | Gly | Tyr | Nle | Leu | Cys | His | Hyp | Cys | |
| 183 | | Asn | Gly | Val | Cys | Cys | DGlu | Tyr | Lys | Leu | Cys | His | Pro | Cys | |
| 184 | Tyr | Asn | Gly | Val | Cys | Cys | Gly | Asn | Lys | Leu | Cys | His | Pro | Cys | |
| 185 | | Asn | Gly | Val | Cys | Cys | Gly | Tyr | Nle | Leu | Cys | His | Pro | Cys | |
| 186 | | Asn | Gly | Val | Cys | Cys | Ser | Tyr | Lys | Leu | Cys | His | Pro | Cys | |
| 187 | | pGlu | Gly | Val | Cys | Cys | Gly | Trp | Lys | Leu | Cys | His | Hyp | Cys | |
| 188 | | Asn | Gly | Val | Cys | Cys | DSer | Tyr | Lys | Leu | Cys | His | Pro | Cys | |
| 189 | | pGlu | Gly | Val | Cys | Cys | Gly | Tyr | Cit | Leu | Cys | His | Hyp | Cys | |
| 190 | | Asn | Gly | Val | Cys | Cys | Gly | Tyr | Lys | Leu | Cys | Ala | Hyp | Cys | |
| 191 | | Asn | Gly | Val | Cys | Cys | Gly | Tic | Lys | Leu | Cys | His | Pro | Cys | |
| 192 | | Asn | Gly | Val | Cys | Cys | DPhe | Tyr | Lys | Leu | Cys | His | Pro | Cys | |
| 193 | | | Gly | Ile | Cys | Cys | Gly | Val | Ser | Phe | Cys | Tyr | Hyp | Cys | |
| 194 | | Asn | Gly | Val | Cys | Cys | Gly | Tyr | Gln | Leu | Cys | His | Pro | Cys | |
| 195 | Tyr | Asn | Gly | Val | Cys | Cys | Gly | Glu | Lys | Leu | Cys | His | Pro | Cys | |
| 196 | | Asn | Gly | Val | Cys | Cys | Gly | Tyr | Lys | Lys | Cys | His | Pro | Cys | |
| 197 | | pGlu | Gly | Val | Cys | Cys | Gly | Glu | Lys | Leu | Cys | His | Hyp | Cys | |
| 198 | | pGlu | Gly | Val | Cys | Cys | Gly | Ile | Lys | Leu | Cys | His | Hyp | Cys | |
| 199 | | | Arg | Asn | Cys | Cys | Arg | Leu | Gln | Val | Cys | — | — | Cys | Gly |
| 200 | | Val | Gly | Val | Asp | Asp | Gly | Tyr | Lys | Leu | Cys | His | Hyp | Cys | |
| 201 | Tyr | Asn | Gly | Val | Cys | Cys | Gly | Lys | Lys | Leu | Cys | His | Pro | Cys | |
| 202 | | Asn | Gly | Val | Cys | Cys | Gly | Tyr | Lys | Ala | Cys | His | Hyp | Cys | |
| 203 | | Asn | Gly | Val | Cys | Cys | Gly | Tyr | Ala | Leu | Cys | His | Hyp | Cys | |

TABLE 3-continued

| SEQ ID. NO. | Xaa1 | Xaa2 | Xaa3 | Xaa4 | Cys | Cys | Gly | Tyr | Lys | Leu | Cys | Xaa5 | Xaa6 | Cys |
|---|---|---|---|---|---|---|---|---|---|---|---|---|---|---|
| 204 | Asn | Gly | Val | Cys | Cys | Gly | Ala | Lys | Leu | Cys | His | Hyp | Cys | |
| 205 | Asn | Gly | Val | Cys | Cys | Ala | Tyr | Lys | Leu | Cys | His | Hyp | Cys | |
| 206 | Asn | Gly | Val | Cys | Cys | Gly | DMD | Lys | Leu | Cys | His | Pro | Cys | |
| 207 | Tyr | Asn | Gly | Val | Cys | Cys | Gly | Tyr | Lys | Leu | Cys | Arg | Pro | Cys |
| 208 | Tyr | Asn | Gly | Val | Cys | Cys | Gly | Tyr | Ile | Leu | Cys | His | Pro | Cys |
| 209 | Tyr | Asn | Gly | Val | Cys | Cys | Gly | Tyr | Lys | Asp | Cys | His | Pro | Cys |
| 210 | Tyr | Asn | Gly | Val | Cys | Cys | Gly | Tyr | Lys | Leu | Cys | Glu | Pro | Cys |
| 211 | Tyr | Asn | Gly | Val | Cys | Cys | Gly | Tyr | Trp | Leu | Cys | His | Pro | Cys |
| 212 | Tyr | Asn | Gly | Val | Cys | Cys | Gly | Tyr | Tyr | Leu | Cys | His | Pro | Cys |
| 213 | Asn | Gly | Val | Cys | Cys | Gly | DMD | Lys | Leu | Cys | His | Hyp | Cys | |
| 214 | Asn | Gly | Val | Cys | Cys | Gly | DPA | Lys | Leu | Cys | His | Hyp | Cys | |
| 215 | Asn | Gly | Val | Cys | Cys | Gly | DMK | Lys | Leu | Cys | His | Hyp | Cys | |

Example 2

Binding Studies

The binding activity at the human noradrenaline transporter (hNET) and noradrenaline (NA) uptake were measured for several peptides according to the invention, as well as for MrIA and other peptides not according to the invention.

(i) hNET Radioligand Assay

The ability of χ-conotoxins to act as inhibitors of the human noradrenaline transporter (hNET) can be measured by competitive inhibition of $^3$H-nisoxetine from membrane prepared from COS-7 mammalian cells expressing hNET. Similar results were obtained with other $^3$H-small molecules, such as maxindole.

COS-7 cells (ATCC) grown in 150 mm dishes containing DMEM and 10% serum were transiently transfected with plasmid DNA encoding mammalian (human) NET (Percy et al 1999, Br J Pharmacol 128: 774-780) using metafectene reagent (Biontex). Cells were harvested 48 hrs post transfection, cells were scraped, washed, homogenised and centrifuged using TEM buffer. For each 150 mm dish membrane was resuspended in 500 µL TEM with 10% glycerol. BCA protein estimates were performed giving ≈6 µg/µL. 1 µL membrane+49 µL assay buffer was used per well in the assay (assay buffer is 20 mM Tris HCl pH 7.4, 75 mM NaCl, 0.1 mM EDTA, 0.1 mM EGTA, 0.1% BSA). Total assay volume was 150 µL and each data point performed in triplicate. Peptides at various concentrations ($10^{-4}$ to $10^{-11}$ M) or control ligand (nisoxetine) were added to the assay plate followed by 4.3 nM $^3$H-nisoxetine (Perkin Elmer cat # NET1084). Finally the membrane was added and the assay was incubated for 1 hr at RT after which the reaction was filtered onto GF filtermats B (Perkin Elmer cat #: 1450-521) pretreated with 0.6% PEI using a Tomtec cell harvester and washed 3 times using wash buffer (20 mM HEPES pH 7.4, 125 mM NaCl @ 4° C.). Filtermats were then dried, placed in a filter bag, 9 mLs betaplate scintillant (Perkin Elmer cat # 1205-440) added and filtermats counted on a Wallac MicroBeta instrument. Each data point was performed in triplicate and the results summarised in Table 4 are from n≧3 experiments.

(ii) NA Uptake Assay

The ability of χ-conotoxins to act as inhibitors of the human noradrenaline transporter (hNET) was also measured by non-competitive inhibition of the function of noradrenaline transporter to transport $^3$H-noradrenaline into COS-7 mammalian cells expressing hNET.

COS-7 cells (ATCC) grown in 24 well plates containing DMEM and 10% serum were transiently transfected with plasmid DNA encoding mammalian (human) NET using metafectene reagent (Biontex). Uptake assays were performed at RT 48 hrs post transfection in transport buffer containing 125 mM NaCl, 4.8 mM KCl, 1.2 mM MgSO$_4$, 1.2 mM KH$_2$PO$_4$, 1.3 mM CaCl$_2$, 25 mM HEPES pH7.4, 5.55 mM glucose, 1.02 mM ascorbic acid, 10 µM U-0521 and 100 µM pargyline; Total assay volume was 250 µL. Cells was 3 times with warm PBS followed by the addition of assay buffer. To which was added control or competing ligand at various concentrations ($10^{-4}$ to $10^{-11}$ M). Assay was incubated for 20 mins after which 100 nM 3H-noradrenaline was added and allowed to incubate for 10 mins. Assay stopped by removal and washing with cold PBS. Cells lysed with 500 µL 0.1% SDS, 0.1N NaCl. 100 µL aliquots taken and added to flexible 96 well plate (for the counter) to which supermix scintillant was added (100 µL), mixed well and counted for 3 mins per well. Each data point was performed in triplicate and the results, summarised in Table 4, are from n≧3 experiments. NT=not tested.

TABLE 4

| SEQ ID. NO. | Av IC50 Displacement of 3H-nisoxetine from hNET | AvIC50 Inhibition of NA uptake via hNET |
| --- | --- | --- |
| 13 | −7.85 | −7.60 |
| 14 | −7.80 | −7.48 |
| 15 | −7.66 | −7.33 |
| 16 | −7.54 | −7.44 |
| 17 | −7.55 | −7.21 |
| 18 | −7.46 | −7.29 |
| 19 | −7.45 | −7.35 |
| 20 | −7.42 | −7.59 |
| 21 | −7.40 | NT |
| 22 | −7.37 | −7.09 |
| 23 | −7.35 | −7.21 |
| 24 | −7.35 | NT |
| 25 | −7.32 | NT |
| 26 | −7.30 | NT |
| 27 | −7.25 | −7.24 |
| 28 | −7.14 | −7.16 |
| 29 | −7.13 | NT |
| 30 | −7.07 | NT |
| 31 | −7.06 | NT |
| 32 | −7.06 | −7.16 |
| 33 | −7.06 | NT |
| 34 | −7.05 | NT |
| 35 | −7.02 | NT |
| 36 | −7.01 | −7.07 |
| 37 | −7.00 | NT |
| 38 | −6.99 | NT |
| 39 | −6.99 | NT |
| 40 | −6.98 | NT |
| 41 | −6.96 | −6.88 |
| 42 | −6.93 | −7.33 |
| 43 | −6.91 | NT |
| 44 | −6.89 | NT |
| 45 | −6.88 | −6.93 |
| 46 | −6.88 | NT |
| 47 | −6.88 | −6.78 |
| 48 | −6.88 | −7.17 |
| 49 | −6.87 | NT |
| 50 | −6.86 | NT |
| 51 | −6.84 | −7.11 |
| 52 | −6.83 | −7.09 |
| 53 | −6.81 | −6.84 |
| 54 | −6.80 | NT |
| 55 | −6.78 | −6.77 |
| 56 | −6.78 | −7.10 |
| 57 | −6.77 | −6.94 |
| 58 | −6.76 | NT |
| 59 | −6.76 | NT |
| 60 | −6.75 | NT |
| 61 | −6.75 | −6.90 |
| 62 | −6.74 | NT |
| 63 | −6.72 | NT |
| 64 | −6.72 | NT |
| 65 | −6.71 | NT |
| 66 | −6.70 | −7.04 |
| 67 | −6.69 | −7.12 |
| 68 | −6.66 | NT |
| 69 | −6.66 | NT |
| 70 | −6.65 | NT |
| 71 | −6.64 | −7.42 |
| 72 | −6.62 | −7.22 |
| 73 | −6.60 | NT |
| 74 | −6.60 | −6.67 |
| 75 | −6.60 | NT |
| 76 | −6.58 | NT |
| 77 | −6.56 | −6.91 |
| 78 | −6.56 | NT |
| 79 | −6.56 | −7.11 |
| 80 | −6.55 | −6.87 |
| 81 | −6.53 | NT |
| 82 | −6.53 | −5.50 |
| 83 | −6.52 | NT |
| 84 | −6.52 | NT |
| 85 | −6.51 | −7.05 |
| 86 | −6.50 | −6.96 |
| 87 | −6.48 | NT |

TABLE 4-continued

| SEQ ID. NO. | Av IC50 Displacement of 3H-nisoxetine from hNET | AvIC50 Inhibition of NA uptake via hNET |
|---|---|---|
| 88 | −6.48 | −6.87 |
| 89 | −6.47 | −6.95 |
| 90 | −6.45 | NT |
| 91 | −6.41 | NT |
| 92 | −6.39 | −7.44 |
| 93 | −6.39 | NT |
| 94 | −6.37 | NT |
| 95 | −6.36 | NT |
| 96 | −6.33 | −6.54 |
| 97 | −6.30 | NT |
| 98 | −6.29 | NT |
| 99 | −6.29 | −6.99 |
| 100 | −6.19 | NT |
| 101 | −6.16 | NT |
| 102 | −6.15 | NT |
| 103 | −6.15 | −6.50 |
| 104 | −6.14 | NT |
| 105 | −6.12 | NT |
| 106 | −6.09 | NT |
| 107 | −6.08 | −6.66 |
| 108 | −6.06 | NT |
| 109 | −6.03 | NT |
| 110 | −6.01 | NT |
| 111 | −6.01 | NT |
| 112 | −5.99 | NT |
| 113 | −5.96 | NT |
| 114 | −5.96 | NT |
| 115 | −5.95 | −6.61 |
| 116 | −5.95 | NT |
| 117 | −5.94 | NT |
| 118 | −5.93 | NT |
| 119 | −5.93 | −6.32 |
| 120 | −5.91 | NT |
| 121 | −5.88 | −6.34 |
| 122 | −5.88 | NT |
| 123 | −5.87 | −6.45 |
| 124 | −5.87 | NT |
| 125 | −5.85 | NT |
| 126 | −5.81 | −6.32 |
| 127 | −5.81 | −6.46 |
| 128 | −5.79 | −6.28 |
| 129 | −5.79 | NT |
| 130 | −5.78 | NT |
| 131 | −5.75 | NT |
| 1 (MrIA) | −5.74 | −6.30 |
| 132 | −5.74 | NT |
| 133 | −5.74 | −6.30 |
| 134 | −5.74 | NT |
| 135 | −5.71 | −6.31 |
| 7 (Mar2) | −5.69 | NT |
| 136 | −5.68 | −6.34 |
| 137 | −5.67 | NT |
| 138 | −5.64 | NT |
| 139 | −5.64 | −6.36 |
| 140 | −5.64 | −6.58 |
| 141 | −5.61 | NT |
| 142 | −5.60 | −6.20 |
| 143 | −5.59 | NT |
| 144 | −5.56 | NT |
| 145 | −5.53 | NT |
| 146 | −5.51 | −6.13 |
| 147 | −5.50 | NT |
| 148 | −5.50 | −6.46 |
| 149 | −5.48 | NT |
| 150 | −5.46 | −6.01 |
| 151 | −5.45 | NT |
| 152 | −5.44 | NT |
| 153 | −5.43 | NT |
| 154 | −5.40 | NT |
| 155 | −5.39 | NT |
| 156 | −5.37 | NT |
| 157 | −5.33 | −6.12 |
| 158 | −5.33 | NT |
| 159 | −5.31 | NT |
| 160 | −5.30 | −6.04 |

TABLE 4-continued

| SEQ ID. NO. | Av IC50 Displacement of 3H-nisoxetine from hNET | AvIC50 Inhibition of NA uptake via hNET |
|---|---|---|
| 161 | -5.21 | NT |
| 162 | -5.19 | NT |
| 163 | -5.16 | NT |
| 164 | -5.16 | NT |
| 165 | -5.15 | NT |
| 166 | -5.35 | NT |
| 167 | -5.07 | -5.84 |
| 168 | -5.04 | -5.58 |
| 169 | -5.03 | NT |
| 170 | -5.00 | NT |
| 171 | -4.97 | NT |
| 172 | -4.97 | NT |
| 173 | -4.89 | -5.38 |
| 174 | -4.76 | NT |
| 175 | -4.74 | NT |
| 176 | -4.71 | NT |
| 177 | -4.64 | NT |
| 178 | -4.63 | NT |
| 179 | -4.60 | NT |
| 180 | -4.53 | NT |
| 181 | -4.32 | NT |
| 182 | -4.24 | NT |
| 183 | -4.21 | NT |
| 184 | -4.10 | NT |
| 185 | -4.09 | NT |
| 186 | -4.04 | NT |
| 187 | -4.04 | NT |
| 188 | -4.02 | NT |
| 189 | -4.02 | NT |
| 190 | -3.99 | -5.10 |
| 191 | -3.96 | NT |
| 192 | -3.95 | NT |
| 193 | -3.92 | NT |
| 194 | -3.91 | NT |
| 195 | -3.77 | NT |
| 196 | -3.74 | NT |
| 197 | -3.72 | NT |
| 198 | -3.67 | NT |
| 199 | -3.62 | NT |
| 200 | -3.55 | NT |
| 201 | -3.36 | NT |
| 202 | -2.00 | NT |
| 203 | -2.00 | -4.86 |
| 204 | -2.00 | NT |
| 205 | -2.00 | NT |
| 206 | -2.00 | NT |
| 207 | -2.00 | NT |
| 208 | -2.00 | NT |
| 209 | -2.00 | NT |
| 210 | -2.00 | NT |
| 211 | -2.00 | NT |
| 212 | -2.00 | NT |
| 213 | -2.00 | -5.40 |
| 214 | -2.00 | -5.41 |
| 215 | -2.00 | -6.77 |

Example 3

Antinociceptive Efficacy of SEQ ID NO. 20 in Rats with Neuropathic Pain Secondary to a Chronic Constriction Injury of the Sciatic Nerve Method Animals Adult male Sprague-Dawley rats were purchased from the Animal Resources Centre (ARC), Perth, Australia, and the Herston Medical Research Centre, The University of Queensland. Rats were housed in a temperature controlled environment (21±2EC) with a 12 h/12 h light/dark cycle. Food and water were available ad libitum. Ethical approval for this study was obtained from the Animal Experimentation Ethics Committee of The University of Queensland.

Reagents and Materials

Isoflurane (Forthane) was obtained from Abbott Australasia Pty Ltd (Sydney, Australia). Sodium benzylpenicillin vials (600 mg) were purchased from CSL Ltd (Melbourne, Australia). Normal saline ampoules were obtained from Delta West Pty Ltd (Perth, Australia) and heparinised saline (50 IU/5 ml) was purchased from Astra Pharmaceuticals Pty Ltd (Sydney, Australia). Single lumen polyethylene tubing (I.D. 0.2 mm, O.D. 0.6 mm) was purchased from Auburn Plastics and Engineering Pty Ltd (Sydney, Australia). Sterile siliconized silk sutures (Dysilk™) were obtained from Dynek Pty Ltd (Adelaide, South Australia) and Michel clips were purchased from Medical and Surgical Requisites Pty Ltd (Brisbane, Australia).

Chronic Constriction Injury (CCI) of the Sciatic Nerve

Rats were anaesthetised with ketamine (80 mg/kg) and xylazine (8 mg/kg) administered by intraperitoneal injection, and a chronic constriction injury (CCI) of the sciatic nerve was produced according to the method of Bennett and Xie (1988). Briefly, the left common sciatic nerve was exposed at mid-thigh level by blunt dissection through the biceps femoris. Proximal to the trifurcation, ~10 mm of nerve was freed of adhering tissue and four loose ligatures (3.0 silk) were tied around the sciatic nerve (~1 mm apart). The incision was closed in layers. After surgery, rats received benzylpenicillin (60 mg s.c.) to prevent infection and were kept warm during surgical recovery. Rats were housed singly for 14 days prior to opioid or vehicle administration. Rats were inspected daily from the time of CCI-surgery with regard to posture of the affected hindpaw, exploring behaviour, body weight and water intake, and any signs of autotomy.

Intrathecal Catheter Insertion

Ten to eleven days post CCI-surgery or in untreated controls, rats were deeply anaesthetised with a mixture of ketamine (80 mg kg$^{-1}$) and xylazine (8 mg/kg) administered as a single intraperitoneal (i.p.) injection. Prior to surgery, the back and neck regions of the rat were shaved and the skin cleansed with betadine surgical scrub. The rat was then placed in a prone position and the L6 lumbar vertebra was located by palpation of the tuber sacrales of the os ileum (Hebel & Stromberg 1976). A 6 cm incision was made in the midline of the back, 3 cm caudal and 3 cm cephalad to L6. A subcutaneous pocket (for the intrathecal catheter) was formed by blunt dissection with scissors on both sides of the incision. The fascia covering the superficial muscles of the back were cut in a 5 mm V-shaped incision that encompassed L5. Additional 5 mm caudal incisions were made parallel to L6. The fascia was then retracted and the lumbar muscles surrounding the base of L5 and L6 were removed, as was the m. interspinalis between the spinous processes of L5-L6.

Following removal of the L6 spinous processes with rongeurs, the soft tissue beneath the L5 iliac arch was removed, exposing the dura mater. The dural membrane was pierced with a 23G needle, releasing clear CSF. A polyethylene catheter (O.D. 0.6 mm, I.D. 0.2 mm; 20 cm in length) pre-filled with saline, was carefully advanced a distance of 1 cm into the intrathecal space and a small volume of saline (20 mL) was administered through the catheter. If leakage of saline around the catheter was observed, the rat was excluded from further experimentation. After successful completion of the 'leak test', the intrathecal (i.t.) catheter was fixed with dental cement onto the surrounding muscle ~2 cm from L5, exteriorised through a subcutaneous (s.c.) tunnel to a small incision at the base of the neck and sutured in position. After suturing of the lumbar muscles and skin, rats received benzylpenicillin (50000 IU i.p.) and enrofloxacin (5 mg·kg$^{-1}$ s.c.) to prevent infection and were kept warm during recovery from anaesthesia. Following completion of the surgery, rats were housed singly for a recovery period of 3-4 days prior to i.t. drug administration. On the day following surgery, the local anaesthetic, lignocaine (2%, 20 mL) was administered via the i.t. catheter. If complete paralysis of both hind legs was not observed, rats were excluded from further experimentation.

Drugs Administered

SEQ ID NO. 20 was prepared in 5 mM sodium acetate buffer at pH 5.5 at delivered to rats in a single bolus dose of 0.2-30 mmoles. Stock solutions of the peptides were quantified relative to an amino acid analysed stock solution by reversed phase HPLC with u.v. detection at Xenome Ltd. The effects of SEQ ID NO. 20 were compared to the effects of MrIA.

Storage of Stock Solutions

Aliquots (10 µL) of stock solutions were stored at −20° C. prior to use for animal experimentation. Immediately prior to experimentation, aliquots of the relevant compound were thawed at room temperature and then diluted to the required concentration with sterile saline to achieve the desired final concentration for subsequent i.t. Unused portions were discarded to waste to ensure that compounds only underwent one freeze-thaw cycle.

Intrathecal Drug Dosing

On day 14 post-CCI surgery, individual groups of drug-naïve-CCI rats received an i.t. bolus injection of SEQ ID NO. 20, morphine or saline in a volume of 10-15 µL. Antinociception was assessed using von Frey filaments until responses retuned to baseline (see below for details).

Assessment of Antinociception: CCI Rats Using von Frey Filaments

Tactile allodynia, the distinguishing feature of neuropathic pain, was quantified using von Frey filaments which were used to apply a non-noxious mechanical stimulus (light pressure) to the hindpaw. Rats were transferred to wire mesh testing cages (20 cm×20 cm×20 cm) and allowed to acclimatise for 10 min. Von Frey filaments were used to determine the lowest mechanical threshold required for a brisk paw withdrawal reflex. Briefly, starting with the von Frey filament that produced the lowest force, the filament was applied to the plantar surface of the hindpaw until the filament buckled slightly. Absence of a response after 5 s prompted use of the next filament of increasing weight. Filaments used produced a buckling weight of 2, 4, 6, 8, 10, 12, 14, 16, 18 and 20 g and these were calibrated regularly. A score of 20 g was given to animals that did not respond to any of the von Frey filaments. Paw withdrawal thresholds (g) were converted to area under the curve (AUCh). The maximum response on the ipsilateral side was 45 AUCh Verification of Correct i.t. Catheter Placement At the completion of each experiment, malachite green dye (30 µL) was injected via the i.t. catheter whilst rats were lightly anaesthetised with $O_2$:$CO_2$ (50%:50%). Thirty seconds later, rats were decapitated and the spinal column was exposed surgically. Data from rats where there was evidence of subcutaneous dye leakage at the site where the catheter entered the back muscles above L6 or failure of the dye to distribute at least 3-4 cm along the spinal cord, were excluded from the analysis.

Data Analysis

The area under the degree of antinociception versus time curve (AUC values) for each peptide was calculated from time=0 to 3 h. Dose-response curves for each peptide was constructed by plotting AUC values versus the i.t. peptide dose (expressed in nmol per rat).

Results

Seq Id No. 20 (0.1 and 0.2 mmol, n=3 per dose) given by the i.t. route produced dose-dependent relief of tactile allodynia (defining symptom of neuropathic pain) in rats with a chronic constriction injury of the sciatic nerve. The mean (±SEM) paw withdrawal threshold versus time curves evoked by i.t. Seq Id No. 20 (0.1 and 0.2 mmol) for the relief of tactile allodynia (hypersensitivity to the non-noxious stimulus of light pressure) in the ipsilateral hindpaw of rats with a chronic constriction injury (CCI) of the sciatic nerve are shown in FIG. 1.

Seq Id No. 20 produced robust antinociception in CCI-rats that appeared to be dose-dependent in the ipsilateral hindpaw and which peaked at 0.75 h post-dosing. Moreover, the anti-allodynic effect was long-lasting (>3 h) and 50-fold more potent than MrIA. This is consistent with results from the NET uptake assay, where Seq Id No. 20 was 20-fold more potent than MrIA at inhibiting NA uptake. Similarly, dose-dependent antinociception was observed in the contralateral (non-injured) paw, however, the paw withdrawal threshold in the ipsilateral paw are approximately half those in the contralateral paw. Due to the fact that the baseline paw withdrawal thresholds are approximately 13 g in the contralateral hindpaw (non-injured side) versus approximately 5.5 g in the ipsilateral hindpaw, Seq Id No. 20 increased paw withdrawal thresholds in the contralateral hindpaw to the maximum values (20 g) in this nociceptive test for approximately 1.5 h post-dosing. Importantly, close inspection of the paw withdrawal threshold versus time curves for the ipsilateral and contralateral hindpaws following intrathecal administration of Seq Id No. 20 in the low dose (0.1 mmol), suggests that this compound has a more pronounced antinociceptive effect in the ipsilateral hindpaw.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

SEQUENCE LISTING

```
<160> NUMBER OF SEQ ID NOS: 215

<210> SEQ ID NO 1
<211> LENGTH: 13
<212> TYPE: PRT
<213> ORGANISM: Conus marmoreus
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 1

Asn Gly Val Cys Cys Gly Tyr Lys Leu Cys His Xaa Cys
1               5                   10

<210> SEQ ID NO 2
<211> LENGTH: 13
<212> TYPE: PRT
<213> ORGANISM: Conus marmoreus
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 2

Val Gly Val Cys Cys Gly Tyr Lys Leu Cys His Xaa Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: synthetic
```

```
<220> FEATURE:
<221> NAME/KEY: MISC_FEATURE
<222> LOCATION: (8)..(9)
<223> OTHER INFORMATION: Xaa is independently absent or represent any
      amino acid residue except Cys

<400> SEQUENCE: 3

Cys Cys Gly Tyr Lys Leu Cys Xaa Xaa Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is selected from Trp, DTrp, Tyr, Phe, hPhe,
      Ala, O-methyl-L-tyrosine, Arg, benzoyl, naphthyl, ornithine, L or
      D pyroglutamic acid and a deletion
<220> FEATURE:
<221> NAME/KEY: MISC_FEATURE
<222> LOCATION: (2)..(2)
<223> OTHER INFORMATION: Xaa is selected from Arg, Ala, Asn, Lys, Phe,
      L-beta-homolysine, L-ornithine, Lys, DArg, L-norleucine, Dlys,
      L-Lysine(dimethyl), DAsn, Thr, 2-aminobenzoyl (anthraniloyl),
      naphthyl, L-citrulline, Val, Tyr, Trp, L or D-pyroglutamic acid
      or a deletion
<220> FEATURE:
<221> NAME/KEY: MISC_FEATURE
<222> LOCATION: (3)..(3)
<223> OTHER INFORMATION: Xaa is selected from Gly, Asp, Lys, Arg, Ala,
      Nle, Ser or Phe
<220> FEATURE:
<221> NAME/KEY: MISC_FEATURE
<222> LOCATION: (4)..(4)
<223> OTHER INFORMATION: Xaa is selected from Val, Leu, Nle, Ile, Thr,
      Ala, Asn, Trp, Phe and Abu
<220> FEATURE:
<221> NAME/KEY: MISC_FEATURE
<222> LOCATION: (12)..(13)
<223> OTHER INFORMATION: Xaa are independently absent or represent any
      amino acid residue except Cys

<400> SEQUENCE: 4

Xaa Xaa Xaa Xaa Cys Cys Gly Tyr Lys Leu Cys Xaa Xaa Cys
1               5                   10

<210> SEQ ID NO 5
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is selected from L or D-pyroglutamic acid,
      Pro, 4-hydroxyproline or an N-acetylated amino acid residue
<220> FEATURE:
<221> NAME/KEY: MISC_FEATURE
<222> LOCATION: (2)..(2)
<223> OTHER INFORMATION: Xaa is selected from Arg, DArg, Asn, DAsn, Lys,
      Thr, DLys, L-beta-homolysine, L-ornithine, L-norleucine,
      L-lysine(dimethyl), 2-aminobenzoyl(anthraniloyl), naphthyl,
      L-citrulline, Val and a deletion
<220> FEATURE:
<221> NAME/KEY: MISC_FEATURE
<222> LOCATION: (3)..(3)
<223> OTHER INFORMATION: Xaa is selected from Gly, Asp, Lys, Arg, Ala,
      L-norleucine and Ser
<220> FEATURE:
<221> NAME/KEY: MISC_FEATURE
```

```
<222> LOCATION: (4)..(4)
<223> OTHER INFORMATION: Xaa is selected from Val, Leu, L-norleucine,
      Ile, Thr, Ala and L-alpha-aminobutyric acid
<220> FEATURE:
<221> NAME/KEY: MISC_FEATURE
<222> LOCATION: (12)..(13)
<223> OTHER INFORMATION: Xaa are independently absent or represent any
      amino acid residue except Cys

<400> SEQUENCE: 5

Xaa Xaa Xaa Xaa Cys Cys Gly Tyr Lys Leu Cys Xaa Xaa Cys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is selected from Arg, DArg,
      L-lysine(dimethyl), L-ornithine or L-beta-homolysine
<220> FEATURE:
<221> NAME/KEY: MISC_FEATURE
<222> LOCATION: (2)..(2)
<223> OTHER INFORMATION: Xaa is selected from Gly, Asp, Lys, Arg, Ala,
      L-norleucine and Ser
<220> FEATURE:
<221> NAME/KEY: MISC_FEATURE
<222> LOCATION: (3)..(3)
<223> OTHER INFORMATION: Xaa is selected from Val, Leu, L-norleucine,
      Ile, Thr, Ala and L-alpha-aminobutyric acid
<220> FEATURE:
<221> NAME/KEY: MISC_FEATURE
<222> LOCATION: (11)..(12)
<223> OTHER INFORMATION: Xaa are independently absent or represent any
      amino acid residue except Cys

<400> SEQUENCE: 6

Xaa Xaa Xaa Cys Cys Gly Tyr Lys Leu Cys Xaa Xaa Cys
1               5                   10

<210> SEQ ID NO 7
<211> LENGTH: 13
<212> TYPE: PRT
<213> ORGANISM: Conus marmoreus
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 7

Gly Val Cys Cys Gly Tyr Lys Leu Cys Cys His Xaa Cys
1               5                   10

<210> SEQ ID NO 8
<211> LENGTH: 11
<212> TYPE: PRT
<213> ORGANISM: Conus marmoreus
<220> FEATURE:
<221> NAME/KEY: MISC_FEATURE
<222> LOCATION: (10)..(10)
<223> OTHER INFORMATION: Xaa is 4-hydroxyproline

<400> SEQUENCE: 8

Val Cys Cys Gly Tyr Lys Leu Cys His Xaa Cys
1               5                   10

<210> SEQ ID NO 9
```

```
<211> LENGTH: 12
<212> TYPE: PRT
<213> ORGANISM: Conus marmoreus
<220> FEATURE:
<221> NAME/KEY: MISC_FEATURE
<222> LOCATION: (11)..(11)
<223> OTHER INFORMATION: Xaa is 4-hydroxyproline

<400> SEQUENCE: 9

Gly Ile Cys Cys Gly Val Ser Phe Cys Tyr Xaa Cys
1               5                   10

<210> SEQ ID NO 10
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (11)..(11)
<223> OTHER INFORMATION: AMIDATION

<400> SEQUENCE: 10

Ala Cys Cys Gly Tyr Lys Leu Cys Ser Pro Cys
1               5                   10

<210> SEQ ID NO 11
<211> LENGTH: 13
<212> TYPE: PRT
<213> ORGANISM: Artificial Sequence
<220> FEATURE:
<223> OTHER INFORMATION: synthetic

<400> SEQUENCE: 11

Asn Gly Val Cys Cys Gly Tyr Lys Leu Cys Leu Pro Cys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: synthetic

<400> SEQUENCE: 12

Ser Val Cys Cys Gly Tyr Lys Leu Cys Phe Pro Cys
1               5                   10

<210> SEQ ID NO 13
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 13

Tyr Arg Gly Leu Cys Cys Gly Xaa Lys Leu Cys Arg Xaa Cys
1               5                   10

<210> SEQ ID NO 14
```

<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: Xaa is N-norleucine
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 14

Tyr Arg Gly Xaa Cys Cys Gly Xaa Lys Leu Cys Arg Xaa Cys
1               5                   10

<210> SEQ ID NO 15
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-ornithine
<220> FEATURE:
<221> NAME/KEY: MISC_FEATURE
<222> LOCATION: (5)..(5)
<223> OTHER INFORMATION: Xaa is L-norleucine
<220> FEATURE:
<221> NAME/KEY: MISC_FEATURE
<222> LOCATION: (9)..(9)
<223> OTHER INFORMATION: Xaa is O-methyl-L-tyrosine
<220> FEATURE:
<221> NAME/KEY: MISC_FEATURE
<222> LOCATION: (14)..(14)
<223> OTHER INFORMATION: Xaa is 4-hydroxyproline

<400> SEQUENCE: 15

Xaa Tyr Arg Gly Xaa Cys Cys Gly Xaa Lys Leu Cys Arg Xaa Cys
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 16

Trp Arg Gly Leu Cys Cys Gly Xaa Lys Leu Cys His Xaa Cys
1               5                   10

<210> SEQ ID NO 17
<211> LENGTH: 14
<212> TYPE: PRT
<213> ORGANISM: Artificial Sequence
<220> FEATURE:

```
<223> OTHER INFORMATION: synthetic
<220> FEATURE:
<221> NAME/KEY: MISC_FEATURE
<222> LOCATION: (1)..(1)
<223> OTHER INFORMATION: Xaa is L-ornithine
<220> FEATURE:
<221> NAME/KEY: MISC_FEATURE
<222> LOCATION: (4)..(4)
<223> OTHER INFORMATION: Xaa is L-norleucine
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 17

Xaa Arg Gly Xaa Cys Cys Gly Xaa Lys Leu Cys Arg Xaa Cys
1               5                   10

<210> SEQ ID NO 18
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(5)
<223> OTHER INFORMATION: Xaa is L-norleucine
<220> FEATURE:
<221> NAME/KEY: MISC_FEATURE
<222> LOCATION: (9)..(9)
<223> OTHER INFORMATION: Xaa is O-methyl-L-tyrosine
<220> FEATURE:
<221> NAME/KEY: MISC_FEATURE
<222> LOCATION: (14)..(14)
<223> OTHER INFORMATION: Xaa is 4-hydroxyproline

<400> SEQUENCE: 18

Lys Tyr Arg Gly Xaa Cys Cys Gly Xaa Lys Leu Cys Arg Xaa Cys
1               5                   10                  15

<210> SEQ ID NO 19
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (3)..(3)
<223> OTHER INFORMATION: Xaa is L-norleucine
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (9)..(9)
<223> OTHER INFORMATION: Xaa is L-homoleucine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 19

Xaa Gly Xaa Cys Cys Gly Xaa Lys Xaa Cys His Xaa Cys
```

<210> SEQ ID NO 20
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 20

Trp Arg Gly Val Cys Cys Gly Xaa Lys Leu Cys His Xaa Cys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 21

Trp Lys Gly Val Cys Cys Gly Xaa Lys Leu Cys His Xaa Cys
1               5                   10

<210> SEQ ID NO 22
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(5)
<223> OTHER INFORMATION: Xaa is L-norleucine
<220> FEATURE:
<221> NAME/KEY: MISC_FEATURE
<222> LOCATION: (9)..(9)
<223> OTHER INFORMATION: Xaa is O-methyl-L-tyrosine
<220> FEATURE:
<221> NAME/KEY: MISC_FEATURE
<222> LOCATION: (14)..(14)
<223> OTHER INFORMATION: Xaa is 4-hydroxyproline

<400> SEQUENCE: 22

Phe Arg Tyr Gly Xaa Cys Cys Gly Xaa Lys Leu Cys Arg Xaa Cys
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(2)

```
<223> OTHER INFORMATION: Xaa is L-ornithine
<220> FEATURE:
<221> NAME/KEY: MISC_FEATURE
<222> LOCATION: (5)..(5)
<223> OTHER INFORMATION: Xaa is L-norleucine
<220> FEATURE:
<221> NAME/KEY: MISC_FEATURE
<222> LOCATION: (9)..(9)
<223> OTHER INFORMATION: Xaa is O-methyl-L-tyrosine
<220> FEATURE:
<221> NAME/KEY: MISC_FEATURE
<222> LOCATION: (14)..(14)
<223> OTHER INFORMATION: Xaa is 4-hydroxyproline

<400> SEQUENCE: 23

Tyr Xaa Arg Gly Xaa Cys Cys Gly Xaa Lys Leu Cys Arg Xaa Cys
1               5                   10                  15

<210> SEQ ID NO 24
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is D-tryptophan
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 24

Trp Arg Gly Leu Cys Cys Gly Xaa Lys Leu Cys Arg Ala Cys
1               5                   10

<210> SEQ ID NO 25
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 25

Trp Arg Gly Val Cys Cys Gly Xaa Lys Leu Cys His Xaa Cys
1               5                   10

<210> SEQ ID NO 26
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 26

Trp Arg Gly Leu Cys Cys Gly Tyr Lys Leu Cys His Xaa Cys
1               5                   10
```

```
<210> SEQ ID NO 27
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (3)..(3)
<223> OTHER INFORMATION: Xaa is L-norleucine
<220> FEATURE:
<221> NAME/KEY: MISC_FEATURE
<222> LOCATION: (9)..(9)
<223> OTHER INFORMATION: Xaa is L-homoleucine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 27

Xaa Gly Xaa Cys Cys Gly Tyr Lys Xaa Cys His Xaa Cys
1               5                   10

<210> SEQ ID NO 28
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(5)
<223> OTHER INFORMATION: Xaa is L-norleucine
<220> FEATURE:
<221> NAME/KEY: MISC_FEATURE
<222> LOCATION: (9)..(9)
<223> OTHER INFORMATION: Xaa is O-methyl-L-tyrosine
<220> FEATURE:
<221> NAME/KEY: MISC_FEATURE
<222> LOCATION: (14)..(14)
<223> OTHER INFORMATION: Xaa is 4-hydroxyproline

<400> SEQUENCE: 28

Tyr Phe Arg Gly Xaa Cys Cys Gly Xaa Lys Leu Cys Arg Xaa Cys
1               5                   10                  15

<210> SEQ ID NO 29
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 29

Trp Arg Gly Val Cys Cys Gly Xaa Lys Leu Cys Arg Ala Cys
1               5                   10

<210> SEQ ID NO 30
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
```

<222> LOCATION: (13)..(13)
<223> OTHER INFORMATION: Xaa is 4-hydroxyproline

<400> SEQUENCE: 30

Trp Arg Gly Val Cys Cys Gly Tyr Lys Leu Cys His Xaa Cys
1               5                   10

<210> SEQ ID NO 31
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is O-methyl-L-tyrosine

<400> SEQUENCE: 31

Trp Gly Leu Cys Cys Gly Xaa Lys Leu Cys Arg Tyr Cys
1               5                   10

<210> SEQ ID NO 32
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (3)..(3)
<223> OTHER INFORMATION: Xaa is L-norleucine
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 32

Xaa Gly Xaa Cys Cys Gly Xaa Lys Leu Cys His Xaa Cys
1               5                   10

<210> SEQ ID NO 33
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 33

Trp Asn Gly Val Cys Cys Gly Tyr Lys Leu Cys His Xaa Cys
1               5                   10

<210> SEQ ID NO 34
<211> LENGTH: 14
<212> TYPE: PRT
<213> ORGANISM: Artificial Sequence
<220> FEATURE:
<223> OTHER INFORMATION: synthetic
<220> FEATURE:

```
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 34

Tyr Arg Gly Leu Cys Cys Gly Xaa Lys Leu Cys Arg Xaa Cys
1               5                   10

<210> SEQ ID NO 35
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 35

Trp Gly Leu Cys Cys Gly Xaa Lys Leu Cys Arg Xaa Cys
1               5                   10

<210> SEQ ID NO 36
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 36

Trp Arg Gly Leu Cys Cys Gly Xaa Lys Leu Cys Arg Lys Cys
1               5                   10

<210> SEQ ID NO 37
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 37

Trp Arg Gly Leu Cys Cys Gly Xaa Lys Leu Cys Arg Ala Cys
1               5                   10

<210> SEQ ID NO 38
<211> LENGTH: 14
<212> TYPE: PRT
<213> ORGANISM: Artificial Sequence
<220> FEATURE:
<223> OTHER INFORMATION: synthetic
```

```
<400> SEQUENCE: 38

Trp Arg Gly Val Cys Cys Gly Tyr Lys Leu Cys Arg Ala Cys
1               5                   10

<210> SEQ ID NO 39
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 39

Trp Asn Gly Val Cys Cys Gly Tyr Lys Leu Cys Arg Xaa Cys
1               5                   10

<210> SEQ ID NO 40
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 40

Trp Arg Gly Val Cys Cys Gly Xaa Lys Leu Cys His Ala Cys
1               5                   10

<210> SEQ ID NO 41
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-pyroglutamic acid
<220> FEATURE:
<221> NAME/KEY: MISC_FEATURE
<222> LOCATION: (5)..(5)
<223> OTHER INFORMATION: Xaa is L-norleucine
<220> FEATURE:
<221> NAME/KEY: MISC_FEATURE
<222> LOCATION: (9)..(9)
<223> OTHER INFORMATION: Xaa is O-methyl-L-tyrosine
<220> FEATURE:
<221> NAME/KEY: MISC_FEATURE
<222> LOCATION: (14)..(14)
<220> FEATURE:
<221> NAME/KEY: misc_feature
<222> LOCATION: (14)..(14)
<223> OTHER INFORMATION: Xaa can be any naturally occurring amino acid

<400> SEQUENCE: 41

Xaa Tyr Arg Gly Xaa Cys Cys Gly Xaa Lys Leu Cys Arg Xaa Cys
1               5                   10                  15

<210> SEQ ID NO 42
<211> LENGTH: 13
<212> TYPE: PRT
<213> ORGANISM: Artificial Sequence
<220> FEATURE:
<223> OTHER INFORMATION: synthetic
```

```
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa is L-norleucine
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 42

Xaa Gly Xaa Cys Cys Gly Xaa Lys Xaa Cys His Xaa Cys
1               5                   10

<210> SEQ ID NO 43
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 43

Trp Arg Gly Val Cys Cys Gly Tyr Lys Leu Cys His Xaa Cys Tyr
1               5                   10                  15

<210> SEQ ID NO 44
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<220> FEATURE:
<221> NAME/KEY: misc_feature
<222> LOCATION: (12)..(12)
<223> OTHER INFORMATION: Xaa can be any naturally occurring amino acid

<400> SEQUENCE: 44

Trp Gly Leu Cys Cys Gly Xaa Lys Leu Cys Arg Xaa Cys Tyr
1               5                   10

<210> SEQ ID NO 45
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-ornithine
<220> FEATURE:
```

```
<221> NAME/KEY: MISC_FEATURE
<222> LOCATION: (3)..(3)
<223> OTHER INFORMATION: Xaa is L-norleucine
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 45

Xaa Gly Xaa Cys Cys Gly Xaa Lys Leu Cys His Xaa Cys
1               5                   10

<210> SEQ ID NO 46
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 46

Trp Asn Gly Val Cys Cys Gly Xaa Lys Leu Cys His Xaa Cys
1               5                   10

<210> SEQ ID NO 47
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: Xaa is L-norleucine
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 47

Asn Gly Xaa Cys Cys Gly Xaa Lys Xaa Cys His Xaa Cys
1               5                   10

<210> SEQ ID NO 48
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-ornithine
<220> FEATURE:
```

```
<221> NAME/KEY: MISC_FEATURE
<222> LOCATION: (3)..(3)
<223> OTHER INFORMATION: Xaa is L-norleucine
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 48

Xaa Gly Xaa Cys Cys Gly Xaa Lys Xaa Cys His Xaa Cys
1               5                   10

<210> SEQ ID NO 49
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 49

Xaa Gly Val Cys Cys Gly Tyr Lys Xaa Cys His Xaa Cys
1               5                   10

<210> SEQ ID NO 50
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<223> OTHER INFORMATION: Xaa is L-norleucine
<220> FEATURE:
<221> NAME/KEY: MISC_FEATURE
<222> LOCATION: (4)..(4)
<223> OTHER INFORMATION: Xaa is L-norleucine

<400> SEQUENCE: 50

Tyr Asn Gly Xaa Cys Cys Gly Tyr Lys Leu Cys His Pro Cys
1               5                   10

<210> SEQ ID NO 51
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-ornithine
<220> FEATURE:
<221> NAME/KEY: MISC_FEATURE
```

```
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 51

Xaa Gly Leu Cys Cys Gly Xaa Lys Leu Cys His Xaa Cys
1               5                   10

<210> SEQ ID NO 52
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-ornithine
<220> FEATURE:
<221> NAME/KEY: MISC_FEATURE
<222> LOCATION: (3)..(3)
<223> OTHER INFORMATION: Xaa is L-norleucine
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (12)..(12)
<220> FEATURE:
<221> NAME/KEY: misc_feature
<222> LOCATION: (12)..(12)
<223> OTHER INFORMATION: Xaa can be any naturally occurring amino acid

<400> SEQUENCE: 52

Xaa Gly Xaa Cys Cys Gly Tyr Lys Xaa Cys His Xaa Cys
1               5                   10

<210> SEQ ID NO 53
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 53

Trp Asn Gly Val Cys Cys Gly Xaa Lys Leu Cys His Pro Cys
1               5                   10

<210> SEQ ID NO 54
<211> LENGTH: 14
<212> TYPE: PRT
<213> ORGANISM: Artificial Sequence
<220> FEATURE:
<223> OTHER INFORMATION: synthetic

<400> SEQUENCE: 54

Trp Arg Gly Val Cys Cys Gly Tyr Lys Leu Cys His Ala Cys
1               5                   10

<210> SEQ ID NO 55
<211> LENGTH: 15
<212> TYPE: PRT
<213> ORGANISM: Artificial Sequence
```

```
<220> FEATURE:
<223> OTHER INFORMATION: synthetic
<220> FEATURE:
<221> NAME/KEY: MISC_FEATURE
<222> LOCATION: (5)..(5)
<223> OTHER INFORMATION: Xaa is L-norleucine
<220> FEATURE:
<221> NAME/KEY: MISC_FEATURE
<222> LOCATION: (9)..(9)
<223> OTHER INFORMATION: Xaa is O-methyl-L-tyrosine
<220> FEATURE:
<221> NAME/KEY: MISC_FEATURE
<222> LOCATION: (14)..(14)
<223> OTHER INFORMATION: Xaa is 4-hydroxyproline

<400> SEQUENCE: 55

Asp Tyr Arg Gly Xaa Cys Cys Gly Xaa Lys Leu Cys Arg Xaa Cys
1               5                   10                  15

<210> SEQ ID NO 56
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (10)..(10)
<223> OTHER INFORMATION: Xaa is L-homoleucine

<400> SEQUENCE: 56

Tyr Asn Gly Val Cys Cys Gly Tyr Lys Xaa Cys His Pro Cys
1               5                   10

<210> SEQ ID NO 57
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: Xaa is L-norleucine
<220> FEATURE:
<221> NAME/KEY: MISC_FEATURE
<222> LOCATION: (9)..(9)
<223> OTHER INFORMATION: Xaa is L-norleucine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 57

Asn Gly Xaa Cys Cys Gly Tyr Lys Xaa Cys His Xaa Cys
1               5                   10

<210> SEQ ID NO 58
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (3)..(3)
<223> OTHER INFORMATION: Xaa is L-norleucine
<220> FEATURE:
<221> NAME/KEY: MISC_FEATURE
```

```
<222> LOCATION: (12)..(12)
<223> OTHER INFORMATION: Xaa is 4-hydroxyproline

<400> SEQUENCE: 58

Xaa Gly Xaa Cys Cys Gly Tyr Lys Leu Cys His Xaa Cys
1               5                   10

<210> SEQ ID NO 59
<211> LENGTH: 13
<212> TYPE: PRT
<213> ORGANISM: Artificial Sequence
<220> FEATURE:
<223> OTHER INFORMATION: synthetic

<400> SEQUENCE: 59

Asn Gly Val Cys Cys Gly Tyr Lys Leu Cys Trp Pro Cys
1               5                   10

<210> SEQ ID NO 60
<211> LENGTH: 14
<212> TYPE: PRT
<213> ORGANISM: Artificial Sequence
<220> FEATURE:
<223> OTHER INFORMATION: synthetic

<400> SEQUENCE: 60

Trp Asn Gly Val Cys Cys Gly Tyr Lys Leu Cys Arg Pro Cys
1               5                   10

<210> SEQ ID NO 61
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: Xaa is L-norleucine
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (9)..(9)
<223> OTHER INFORMATION: Xaa is L-norleucine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 61

Asn Gly Xaa Cys Cys Gly Xaa Lys Xaa Cys His Xaa Cys
1               5                   10

<210> SEQ ID NO 62
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 62

Tyr Asn Gly Val Cys Cys Gly Xaa Lys Leu Cys Arg Ala Cys
1               5                   10
```

<210> SEQ ID NO 63
<211> LENGTH: 13
<212> TYPE: PRT
<213> ORGANISM: Artificial Sequence
<220> FEATURE:
<223> OTHER INFORMATION: synthetic

<400> SEQUENCE: 63

Asn Asp Val Cys Cys Gly Tyr Lys Leu Cys His Pro Cys
1               5                   10

<210> SEQ ID NO 64
<211> LENGTH: 14
<212> TYPE: PRT
<213> ORGANISM: Artificial Sequence
<220> FEATURE:
<223> OTHER INFORMATION: synthetic

<400> SEQUENCE: 64

Trp Arg Gly Leu Cys Cys Gly Tyr Lys Leu Cys Arg Gly Cys
1               5                   10

<210> SEQ ID NO 65
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is D-pyroglutamic acid
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 65

Xaa Gly Leu Cys Cys Gly Xaa Lys Leu Cys Arg Xaa Cys Tyr
1               5                   10

<210> SEQ ID NO 66
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-ornithine
<220> FEATURE:
<221> NAME/KEY: MISC_FEATURE
<222> LOCATION: (3)..(3)
<223> OTHER INFORMATION: Xaa is L-norleucine
<220> FEATURE:
<221> NAME/KEY: MISC_FEATURE
<222> LOCATION: (9)..(9)
<223> OTHER INFORMATION: Xaa is L-norleucine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 66

Xaa Gly Xaa Cys Cys Gly Tyr Lys Xaa Cys His Xaa Cys

<210> SEQ ID NO 67
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-homophenylalanine
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 67

Xaa Asn Gly Val Cys Cys Gly Tyr Lys Leu Cys His Xaa Cys
1               5                   10

<210> SEQ ID NO 68
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 68

Tyr Asn Gly Val Cys Cys Gly Tyr Lys Leu Cys Arg Xaa Cys
1               5                   10

<210> SEQ ID NO 69
<211> LENGTH: 14
<212> TYPE: PRT
<213> ORGANISM: Artificial Sequence
<220> FEATURE:
<223> OTHER INFORMATION: synthetic

<400> SEQUENCE: 69

Trp Asn Gly Val Cys Cys Gly Tyr Lys Leu Cys Arg Ala Cys
1               5                   10

<210> SEQ ID NO 70
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<223> OTHER INFORMATION: Xaa is O-methyl-L-tyrosine
<220> FEATURE:
<221> NAME/KEY: MISC_FEATURE
<222> LOCATION: (9)..(9)
<223> OTHER INFORMATION: Xaa is O-methyl-L-tyrosine

<400> SEQUENCE: 70

Phe Gly Gly Phe Trp Cys Cys Gly Xaa Lys Leu Cys Arg Ala Cys
1               5                   10                  15

<210> SEQ ID NO 71
<211> LENGTH: 14
<212> TYPE: PRT
<213> ORGANISM: Artificial Sequence
<220> FEATURE:

```
<223> OTHER INFORMATION: synthetic
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 71

Tyr Asn Gly Val Cys Cys Gly Tyr Lys Leu Cys Trp Xaa Cys
1               5                   10

<210> SEQ ID NO 72
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 72

Trp Asn Gly Leu Cys Cys Gly Tyr Lys Leu Cys His Xaa Cys
1               5                   10

<210> SEQ ID NO 73
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<223> OTHER INFORMATION: Xaa is L-norleucine
<220> FEATURE:
<221> NAME/KEY: MISC_FEATURE
<222> LOCATION: (1)..(1)
<223> OTHER INFORMATION: Xaa is L-ornithine
<220> FEATURE:
<221> NAME/KEY: MISC_FEATURE
<222> LOCATION: (3)..(3)
<223> OTHER INFORMATION: Xaa is L-norleucine

<400> SEQUENCE: 73

Xaa Gly Xaa Cys Cys Gly Tyr Lys Leu Cys His Pro Cys
1               5                   10

<210> SEQ ID NO 74
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: Xaa is L-norleucine
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 74

Asn Gly Xaa Cys Cys Gly Xaa Lys Leu Cys His Xaa Cys
1               5                   10

<210> SEQ ID NO 75
```

```
<211> LENGTH: 13
<212> TYPE: PRT
<213> ORGANISM: Artificial Sequence
<220> FEATURE:
<223> OTHER INFORMATION: synthetic
<210> SEQ ID NO 79
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 79

Xaa Gly Val Cys Cys Gly Xaa Lys Leu Cys His Xaa Cys
1               5                   10

<210> SEQ ID NO 80
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: Xaa is L-norleucine
<220> FEATURE:
<221> NAME/KEY: MISC_FEATURE
<222> LOCATION: (9)..(9)
<223> OTHER INFORMATION: Xaa is L-homoleucine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 80

Asn Gly Xaa Cys Cys Gly Tyr Lys Xaa Cys His Xaa Cys
1               5                   10

<210> SEQ ID NO 81
<211> LENGTH: 14
<212> TYPE: PRT
<213> ORGANISM: Artificial Sequence
<220> FEATURE:
<223> OTHER INFORMATION: synthetic

<400> SEQUENCE: 81

Tyr Asn Gly Val Cys Cys Gly Tyr Lys Leu Cys Arg Ala Cys
1               5                   10

<210> SEQ ID NO 82
<211> LENGTH: 14
<212> TYPE: PRT
<213> ORGANISM: Artificial Sequence
<220> FEATURE:
<223> OTHER INFORMATION: synthetic

<400> SEQUENCE: 82

Trp Asn Gly Val Cys Cys Gly Tyr Lys Leu Cys His Pro Cys
1               5                   10

<210> SEQ ID NO 83
<211> LENGTH: 14
<212> TYPE: PRT

```
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 83

Phe Gly Gly Phe Cys Cys Gly Xaa Lys Leu Cys Arg Ala Cys
1               5                   10

<210> SEQ ID NO 84
<211> LENGTH: 14
<212> TYPE: PRT
<213> ORGANISM: Artificial Sequence
<220> FEATURE:
<223> OTHER INFORMATION: synthetic

<400> SEQUENCE: 84

Tyr Asn Gly Val Cys Cys Gly Tyr Lys Leu Cys Arg Pro Cys
1               5                   10

<210> SEQ ID NO 85
<211> LENGTH: 14
<212> TYPE: PRT
<213> ORGANISM: Artificial Sequence
<220> FEATURE:
<223> OTHER INFORMATION: synthetic

<400> SEQUENCE: 85

Trp Lys Asp Leu Cys Cys Gly Tyr Lys Leu Cys His Pro Cys
1               5                   10

<210> SEQ ID NO 86
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 86

Tyr Asn Gly Val Cys Cys Gly Xaa Lys Leu Cys His Pro Cys
1               5                   10

<210> SEQ ID NO 87
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 87

Xaa Gly Val Cys Cys Gly Tyr Lys Leu Cys Arg Xaa Cys
1               5                   10

<210> SEQ ID NO 88
```

```
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 88

Tyr Asn Gly Val Cys Cys Gly Tyr Lys Leu Cys His Xaa Cys
1               5                   10

<210> SEQ ID NO 89
<211> LENGTH: 14
<212> TYPE: PRT
<213> ORGANISM: Artificial Sequence
<220> FEATURE:
<223> OTHER INFORMATION: synthetic

<400> SEQUENCE: 89

Tyr Asn Gly Val Cys Cys Gly Tyr Lys Leu Cys Arg Pro Cys
1               5                   10

<210> SEQ ID NO 90
<211> LENGTH: 14
<212> TYPE: PRT
<213> ORGANISM: Artificial Sequence
<220> FEATURE:
<223> OTHER INFORMATION: synthetic

<400> SEQUENCE: 90

Trp Lys Asp Leu Cys Cys Gly Tyr Lys Leu Cys Trp Pro Cys
1               5                   10

<210> SEQ ID NO 91
<211> LENGTH: 14
<212> TYPE: PRT
<213> ORGANISM: Artificial Sequence
<220> FEATURE:
<223> OTHER INFORMATION: synthetic

<400> SEQUENCE: 91

Tyr Asn Gly Val Cys Cys Gly Tyr Lys Leu Cys Trp Pro Cys
1               5                   10

<210> SEQ ID NO 92
<211> LENGTH: 14
<212> TYPE: PRT
<213> ORGANISM: Artificial Sequence
<220> FEATURE:
<223> OTHER INFORMATION: synthetic

<400> SEQUENCE: 92

Trp Lys Asp Val Cys Cys Gly Tyr Lys Leu Cys Trp Pro Cys
1               5                   10

<210> SEQ ID NO 93
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-beta-homolysine
```

```
<400> SEQUENCE: 93

Xaa Gly Val Cys Cys Gly Tyr Lys Leu Cys His Pro Cys
1               5                   10

<210> SEQ ID NO 94
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 94

Tyr Asn Gly Val Cys Cys Gly Xaa Lys Leu Cys Pro Cys
1               5                   10

<210> SEQ ID NO 95
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: Xaa is L-beta-homolysine
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 95

Trp Xaa Gly Val Cys Cys Gly Tyr Lys Leu Cys His Xaa Cys
1               5                   10

<210> SEQ ID NO 96
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (3)..(3)
<223> OTHER INFORMATION: Xaa is L-norleucine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 96

Xaa Gly Xaa Cys Cys Gly Tyr Lys Leu Cys His Xaa Cys
1               5                   10

<210> SEQ ID NO 97
<211> LENGTH: 13
<212> TYPE: PRT
<213> ORGANISM: Artificial Sequence
<220> FEATURE:
<223> OTHER INFORMATION: synthetic

<400> SEQUENCE: 97

Asn Gly Leu Cys Cys Gly Tyr Lys Leu Cys His Pro Cys
```

```
<210> SEQ ID NO 98
<211> LENGTH: 13
<212> TYPE: PRT
<213> ORGANISM: Artificial Sequence
<220> FEATURE:
<223> OTHER INFORMATION: synthetic

<400> SEQUENCE: 98

Arg Gly Val Cys Cys Gly Tyr Lys Leu Cys His Pro Cys
1               5                   10

<210> SEQ ID NO 99
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<223> OTHER INFORMATION: Cyclic peptide residue 1 is joined to residue
      13

<400> SEQUENCE: 99

Gly Tyr Lys Leu Gly Cys Cys Gly Tyr Lys Leu Cys Cys
1               5                   10

<210> SEQ ID NO 100
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (15)..(15)
<223> OTHER INFORMATION: Xaa is 4-hydroxyproline

<400> SEQUENCE: 100

Trp Ala Ala Asn Gly Val Cys Cys Gly Tyr Lys Leu Cys His Xaa Cys
1               5                   10                  15

<210> SEQ ID NO 101
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 101

Xaa Gly Val Cys Cys Gly Tyr Lys Leu Cys His Xaa Cys
1               5                   10

<210> SEQ ID NO 102
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
```

```
<222> LOCATION: (12)..(12)
<223> OTHER INFORMATION: Xaa is L-1,2,3,4-tetrahydroisoquinoline-3-
      carboxylic acid

<400> SEQUENCE: 102

Asn Gly Val Cys Cys Gly Tyr Lys Leu Cys His Xaa Cys
1               5                   10

<210> SEQ ID NO 103
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is D-arginine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 103

Xaa Gly Val Cys Cys Gly Tyr Lys Leu Cys His Xaa Cys
1               5                   10

<210> SEQ ID NO 104
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is O-methyl-L-tyrosine

<400> SEQUENCE: 104

Xaa Asn Gly Val Cys Cys Gly Tyr Lys Leu Cys His Pro Cys
1               5                   10

<210> SEQ ID NO 105
<211> LENGTH: 17
<212> TYPE: PRT
<213> ORGANISM: Artificial Sequence
<220> FEATURE:
<223> OTHER INFORMATION: synthetic

<400> SEQUENCE: 105

Gly Ile Leu Arg Asn Gly Val Cys Cys Gly Tyr Lys Leu Cys His Pro
1               5                   10                  15

Cys

<210> SEQ ID NO 106
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (14)..(14)
<223> OTHER INFORMATION: Xaa is 4-hydroxyproline

<400> SEQUENCE: 106

Trp Ala Asn Gly Val Cys Cys Gly Tyr Lys Leu Cys His Xaa Cys
1               5                   10                  15
```

```
<210> SEQ ID NO 107
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-norleucine
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 107

Xaa Gly Val Cys Cys Gly Xaa Lys Leu Cys His Xaa Cys
1               5                   10

<210> SEQ ID NO 108
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<223> OTHER INFORMATION: Xaa is L-ornithine
<220> FEATURE:
<221> NAME/KEY: MISC_FEATURE
<222> LOCATION: (1)..(1)
<223> OTHER INFORMATION: Xaa is L-ornithine

<400> SEQUENCE: 108

Xaa Gly Val Cys Cys Gly Tyr Lys Leu Cys His Pro Cys
1               5                   10

<210> SEQ ID NO 109
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa is L-beta-homolysine
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Xaa is 4-hydroxyproline

<400> SEQUENCE: 109

Trp Xaa Gly Val Cys Cys Gly Tyr Lys Leu Cys His Xaa Cys
1               5                   10
```

```
<210> SEQ ID NO 110
<211> LENGTH: 14
<212> TYPE: PRT
<213> ORGANISM: Artificial Sequence
<220> FEATURE:
<223> OTHER INFORMATION: synthetic

<400> SEQUENCE: 110

Tyr Asn Lys Val Cys Cys Gly Tyr Lys Leu Cys His Pro Cys
1               5                   10

<210> SEQ ID NO 111
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (12)..(12)
<223> OTHER INFORMATION: Xaa is L-1,2,3,4-tetrahydroisoquinoline-3-
      carboxylic acid

<400> SEQUENCE: 111

Xaa Gly Val Cys Cys Gly Tyr Lys Leu Cys His Xaa Cys
1               5                   10

<210> SEQ ID NO 112
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: Xaa is L-norleucine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 112

Asn Gly Xaa Cys Cys Gly Tyr Lys Leu Cys His Xaa Cys
1               5                   10

<210> SEQ ID NO 113
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is O-methyl-L-tyrosine

<400> SEQUENCE: 113

Asn Gly Val Cys Cys Gly Xaa Lys Leu Cys His Pro Cys
1               5                   10

<210> SEQ ID NO 114
<211> LENGTH: 13
<212> TYPE: PRT
<213> ORGANISM: Artificial Sequence
<220> FEATURE:
<223> OTHER INFORMATION: synthetic
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 114

Xaa Gly Val Cys Cys Gly Tyr Lys Leu Cys His Xaa Cys
1               5                   10

<210> SEQ ID NO 115
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 115

Asn Gly Leu Cys Cys Gly Tyr Lys Leu Cys His Xaa Cys
1               5                   10

<210> SEQ ID NO 116
<211> LENGTH: 14
<212> TYPE: PRT
<213> ORGANISM: Artificial Sequence
<220> FEATURE:
<223> OTHER INFORMATION: synthetic

<400> SEQUENCE: 116

Tyr Asn Gly Val Cys Cys Gly Tyr Lys Leu Cys His Pro Cys
1               5                   10

<210> SEQ ID NO 117
<211> LENGTH: 13
<212> TYPE: PRT
<213> ORGANISM: Artificial Sequence
<220> FEATURE:
<223> OTHER INFORMATION: synthetic

<400> SEQUENCE: 117

Asn Gly Val Cys Cys Gly Tyr Lys Leu Cys His Lys Cys
1               5                   10

<210> SEQ ID NO 118
<211> LENGTH: 14
<212> TYPE: PRT
<213> ORGANISM: Artificial Sequence
<220> FEATURE:
<223> OTHER INFORMATION: synthetic

<400> SEQUENCE: 118

Tyr Asn Arg Val Cys Cys Gly Tyr Lys Leu Cys His Pro Cys
1               5                   10

<210> SEQ ID NO 119
<211> LENGTH: 13
<212> TYPE: PRT
<213> ORGANISM: Artificial Sequence
```

```
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-norleucine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 119

Xaa Gly Val Cys Cys Gly Tyr Lys Leu Cys His Xaa Cys
1               5                   10

<210> SEQ ID NO 120
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is benzoyl

<400> SEQUENCE: 120

Xaa Asn Gly Val Cys Cys Gly Tyr Lys Leu Cys His Pro Cys
1               5                   10

<210> SEQ ID NO 121
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is D-lysine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 121

Xaa Gly Val Cys Cys Gly Tyr Lys Leu Cys His Xaa Cys
1               5                   10

<210> SEQ ID NO 122
<211> LENGTH: 13
<212> TYPE: PRT
<213> ORGANISM: Artificial Sequence
<220> FEATURE:
<223> OTHER INFORMATION: synthetic

<400> SEQUENCE: 122

Asn Lys Val Cys Cys Gly Tyr Lys Leu Cys His Pro Cys
1               5                   10

<210> SEQ ID NO 123
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
```

```
<221> NAME/KEY: MISC_FEATURE
<222> LOCATION: (12)..(12)
<223> OTHER INFORMATION: Xaa is 4-hydroxyproline

<400> SEQUENCE: 123

Asn Gly Val Cys Cys Gly Xaa Lys Leu Cys His Xaa Cys
1               5                   10

<210> SEQ ID NO 124
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: Xaa can be any naturally occurring amino acid

<400> SEQUENCE: 124

Asn Ala Val Cys Cys Gly Tyr Lys Leu Cys His Xaa Cys
1               5                   10

<210> SEQ ID NO 125
<211> LENGTH: 13
<212> TYPE: PRT
<213> ORGANISM: Artificial Sequence
<220> FEATURE:
<223> OTHER INFORMATION: synthetic

<400> SEQUENCE: 125

Asn Gly Ile Cys Cys Gly Tyr Lys Leu Cys His Pro Cys
1               5                   10

<210> SEQ ID NO 126
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (9)..(9)
<223> OTHER INFORMATION: Xaa is L-norleucine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 126

Asn Gly Val Cys Cys Gly Tyr Lys Xaa Cys His Xaa Cys
1               5                   10

<210> SEQ ID NO 127
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-Lysine (dimethyl)
<220> FEATURE:
<221> NAME/KEY: MISC_FEATURE
<222> LOCATION: (12)..(12)
<223> OTHER INFORMATION: Xaa is 4-hydroxyproline)

<400> SEQUENCE: 127

Xaa Gly Val Cys Cys Gly Tyr Lys Leu Cys His Xaa Cys
```

```
                 1               5                  10

<210> SEQ ID NO 128
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is D-asparagine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 128

Xaa Gly Val Cys Cys Gly Tyr Lys Leu Cys His Xaa Cys
1               5                   10

<210> SEQ ID NO 129
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is L-Pipecolic acid (homo proline)

<400> SEQUENCE: 129

Asn Gly Val Cys Cys Gly Tyr Lys Leu Cys His Xaa Cys
1               5                   10

<210> SEQ ID NO 130
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 130

Ala Gly Val Cys Cys Gly Tyr Lys Leu Cys His Xaa Cys
1               5                   10

<210> SEQ ID NO 131
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is naphthyl

<400> SEQUENCE: 131

Xaa Asn Gly Val Cys Cys Gly Tyr Lys Leu Cys His Pro Cys
1               5                   10

<210> SEQ ID NO 132
<211> LENGTH: 14
<212> TYPE: PRT
<213> ORGANISM: Artificial Sequence
```

```
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 132

Tyr Asn Xaa Val Cys Cys Gly Tyr Lys Leu Cys His Pro Cys
1               5                   10

<210> SEQ ID NO 133
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 133

Phe Gly Val Cys Cys Gly Tyr Lys Leu Cys His Xaa Cys
1               5                   10

<210> SEQ ID NO 134
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: Xaa is N-Naphthylalanine

<400> SEQUENCE: 134

Asn Gly Val Cys Cys Gly Tyr Lys Leu Cys Xaa Pro Cys
1               5                   10

<210> SEQ ID NO 135
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 135

Thr Gly Val Cys Cys Gly Tyr Lys Leu Cys His Xaa Cys
1               5                   10

<210> SEQ ID NO 136
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is 2-aminobenzoyl (anthraniloyl)
<220> FEATURE:
<221> NAME/KEY: MISC_FEATURE
<222> LOCATION: (12)..(12)
<223> OTHER INFORMATION: Xaa is 4-hydroxyproline
```

```
<400> SEQUENCE: 136

Xaa Gly Val Cys Cys Gly Tyr Lys Leu Cys His Xaa Cys
1               5                   10

<210> SEQ ID NO 137
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is naphthyl

<400> SEQUENCE: 137

Xaa Gly Val Cys Cys Gly Tyr Lys Leu Cys His Pro Cys
1               5                   10

<210> SEQ ID NO 138
<211> LENGTH: 13
<212> TYPE: PRT
<213> ORGANISM: Artificial Sequence
<220> FEATURE:
<223> OTHER INFORMATION: synthetic

<400> SEQUENCE: 138

Asn Gly Thr Cys Cys Gly Tyr Lys Leu Cys His Pro Cys
1               5                   10

<210> SEQ ID NO 139
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-Citrulline
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 139

Xaa Gly Val Cys Cys Gly Tyr Lys Leu Cys His Xaa Cys
1               5                   10

<210> SEQ ID NO 140
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-pyroglutamic acid
<220> FEATURE:
<221> NAME/KEY: MISC_FEATURE
<222> LOCATION: (8)..(8)
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: Xaa is 4-hydroxyproline
```

-continued

```
<400> SEQUENCE: 140

Xaa Asn Gly Val Cys Cys Gly Xaa Lys Leu Cys His Xaa Cys
1               5                   10

<210> SEQ ID NO 141
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is O-methyl-L-tyrosine

<400> SEQUENCE: 141

Asn Gly Val Cys Cys Gly Tyr Lys Leu Cys His Xaa Cys
1               5                   10

<210> SEQ ID NO 142
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-pyroglutamic acid
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 142

Xaa Gly Val Cys Cys Gly Tyr Lys Leu Cys His Xaa Cys
1               5                   10

<210> SEQ ID NO 143
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 143

Asn Gly Val Cys Cys Gly Tyr Lys Leu Cys His Xaa Cys
1               5                   10

<210> SEQ ID NO 144
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is D-pyroglutamic acid
<220> FEATURE:
<221> NAME/KEY: MISC_FEATURE
<222> LOCATION: (12)..(12)
<223> OTHER INFORMATION: Xaa is 4-hydroxyproline
```

```
<400> SEQUENCE: 144

Xaa Gly Val Cys Cys Gly Tyr Lys Leu Cys His Xaa Cys
1               5                   10

<210> SEQ ID NO 145
<211> LENGTH: 13
<212> TYPE: PRT
<213> ORGANISM: Artificial Sequence
<220> FEATURE:
<223> OTHER INFORMATION: synthetic

<400> SEQUENCE: 145

Asn Gly Val Cys Cys Gly Tyr Lys Leu Cys His Ala Cys
1               5                   10

<210> SEQ ID NO 146
<211> LENGTH: 13
<212> TYPE: PRT
<213> ORGANISM: Artificial Sequence
<220> FEATURE:
<223> OTHER INFORMATION: synthetic

<400> SEQUENCE: 146

Asn Gly Val Cys Cys Gly Tyr Lys Leu Cys His Pro Cys
1               5                   10

<210> SEQ ID NO 147
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 147

Asp Gly Val Cys Cys Gly Tyr Lys Leu Cys His Xaa Cys
1               5                   10

<210> SEQ ID NO 148
<211> LENGTH: 9
<212> TYPE: PRT
<213> ORGANISM: Artificial Sequence
<220> FEATURE:
<223> OTHER INFORMATION: synthetic

<400> SEQUENCE: 148

Val Cys Cys Gly Tyr Lys Leu Cys Cys
1               5

<210> SEQ ID NO 149
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is L-dimethyldopa or
      L-dimethoxyphenylalanine

<400> SEQUENCE: 149

Asn Gly Val Cys Cys Gly Tyr Lys Leu Cys His Xaa Cys
1               5                   10
```

```
<210> SEQ ID NO 150
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 150

Asn Gly Ala Cys Cys Gly Tyr Lys Leu Cys His Xaa Cys
1               5                   10

<210> SEQ ID NO 151
<211> LENGTH: 13
<212> TYPE: PRT
<213> ORGANISM: Artificial Sequence
<220> FEATURE:
<223> OTHER INFORMATION: synthetic

<400> SEQUENCE: 151

Asp Gly Val Cys Cys Gly Tyr Lys Leu Cys His Pro Cys
1               5                   10

<210> SEQ ID NO 152
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION

<400> SEQUENCE: 152

Asn Gly Val Cys Cys Gly Tyr Lys Leu Cys His Pro Cys
1               5                   10

<210> SEQ ID NO 153
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 153

Asn Gly Ala Cys Cys Gly Tyr Lys Leu Cys His Xaa Cys
1               5                   10

<210> SEQ ID NO 154
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-pyroglutamic acid
<220> FEATURE:
<221> NAME/KEY: MISC_FEATURE
<222> LOCATION: (12)..(12)
```

```
<223> OTHER INFORMATION: Xaa is 4-hydroxyproline

<400> SEQUENCE: 154

Xaa Asp Val Cys Cys Gly Tyr Lys Leu Cys His Xaa Cys
1               5                   10

<210> SEQ ID NO 155
<211> LENGTH: 13
<212> TYPE: PRT
<213> ORGANISM: Artificial Sequence
<220> FEATURE:
<223> OTHER INFORMATION: synthetic

<400> SEQUENCE: 155

Asn Gly Val Cys Cys Gly Tyr Lys Leu Cys His Phe Cys
1               5                   10

<210> SEQ ID NO 156
<211> LENGTH: 13
<212> TYPE: PRT
<213> ORGANISM: Artificial Sequence
<220> FEATURE:
<223> OTHER INFORMATION: synthetic

<400> SEQUENCE: 156

Asn Ser Val Cys Cys Gly Tyr Lys Leu Cys His Pro Cys
1               5                   10

<210> SEQ ID NO 157
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-pyroglutamic acid
<220> FEATURE:
<221> NAME/KEY: MISC_FEATURE
<222> LOCATION: (13)..(13)
<223> OTHER INFORMATION: Xaa is 4-hydroxyproline

<400> SEQUENCE: 157

Xaa Asn Gly Val Cys Cys Gly Tyr Lys Leu Cys His Xaa Cys
1               5                   10

<210> SEQ ID NO 158
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is L-thiazolidine-4-carboxylic acid

<400> SEQUENCE: 158

Asn Gly Val Cys Cys Gly Tyr Lys Leu Cys His Xaa Cys
1               5                   10

<210> SEQ ID NO 159
<211> LENGTH: 13
<212> TYPE: PRT
<213> ORGANISM: Artificial Sequence
<220> FEATURE:
<223> OTHER INFORMATION: synthetic
```

<400> SEQUENCE: 159

Asn Gly Val Cys Cys Gly Tyr Lys Leu Cys His Glu Cys
1               5                   10

<210> SEQ ID NO 160
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 160

Asn Gly Xaa Cys Cys Gly Tyr Lys Leu Cys His Xaa Cys
1               5                   10

<210> SEQ ID NO 161
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION

<400> SEQUENCE: 161

Tyr Asn Gly Val Cys Cys Gly Tyr Lys Leu Cys His Pro Cys
1               5                   10

<210> SEQ ID NO 162
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is L-norleucine

<400> SEQUENCE: 162

Asn Gly Val Cys Cys Gly Tyr Lys Leu Cys His Xaa Cys
1               5                   10

<210> SEQ ID NO 163
<211> LENGTH: 14
<212> TYPE: PRT
<213> ORGANISM: Artificial Sequence
<220> FEATURE:
<223> OTHER INFORMATION: synthetic

<400> SEQUENCE: 163

Tyr Asn Gly Val Cys Cys Gly Tyr Lys Leu Cys Gln Pro Cys
1               5                   10

<210> SEQ ID NO 164
<211> LENGTH: 13
<212> TYPE: PRT
<213> ORGANISM: Artificial Sequence
<220> FEATURE:

```
<223> OTHER INFORMATION: synthetic
<220> FEATURE:
<221> NAME/KEY: MISC_FEATURE
<222> LOCATION: (1)..(1)
<223> OTHER INFORMATION: Xaa is D-pyroglutamic acid
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 164

Xaa Gly Val Cys Cys Gly Tyr Lys Leu Cys His Xaa Cys
1               5                   10

<210> SEQ ID NO 165
<211> LENGTH: 13
<212> TYPE: PRT
<213> ORGANISM: Artificial Sequence
<220> FEATURE:
<223> OTHER INFORMATION: synthetic

<400> SEQUENCE: 165

Asn Gly Val Cys Cys Gly Tyr Lys Leu Cys His Tyr Cys
1               5                   10

<210> SEQ ID NO 166
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: Xaa is D-lysine

<400> SEQUENCE: 166

Asn Gly Val Cys Cys Xaa Tyr Lys Leu Cys His Pro Cys
1               5                   10

<210> SEQ ID NO 167
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Xaa is L-Lysine (dimethyl)
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 167

Asn Gly Val Cys Cys Gly Tyr Xaa Leu Cys His Xaa Cys
1               5                   10

<210> SEQ ID NO 168
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is L-homotyrosine
<220> FEATURE:
<221> NAME/KEY: MISC_FEATURE
```

```
<222> LOCATION: (12)..(12)
<223> OTHER INFORMATION: Xaa is 4-hydroxyproline

<400> SEQUENCE: 168

Asn Gly Val Cys Cys Gly Xaa Lys Leu Cys His Xaa Cys
1               5                   10

<210> SEQ ID NO 169
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: Xaa is L-3-pyridylalanine

<400> SEQUENCE: 169

Asn Gly Val Cys Cys Gly Tyr Lys Leu Cys Xaa Pro Cys
1               5                   10

<210> SEQ ID NO 170
<211> LENGTH: 14
<212> TYPE: PRT
<213> ORGANISM: Artificial Sequence
<220> FEATURE:
<223> OTHER INFORMATION: synthetic

<400> SEQUENCE: 170

Tyr Asn Gly Val Cys Cys Gly Tyr Lys Leu Cys Lys Pro Cys
1               5                   10

<210> SEQ ID NO 171
<211> LENGTH: 14
<212> TYPE: PRT
<213> ORGANISM: Artificial Sequence
<220> FEATURE:
<223> OTHER INFORMATION: synthetic

<400> SEQUENCE: 171

Tyr Asn Gly Val Cys Cys Gly Leu Lys Leu Cys His Pro Cys
1               5                   10

<210> SEQ ID NO 172
<211> LENGTH: 13
<212> TYPE: PRT
<213> ORGANISM: Artificial Sequence
<220> FEATURE:
<223> OTHER INFORMATION: synthetic

<400> SEQUENCE: 172

Asn Gly Val Cys Cys Gly Tyr Ala Leu Cys His Pro Cys
1               5                   10

<210> SEQ ID NO 173
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (9)..(9)
<223> OTHER INFORMATION: Xaa is 4-hydroxyproline

<400> SEQUENCE: 173

Cys Cys Gly Tyr Lys Leu Cys His Xaa Cys
```

```
1               5                   10
```

<210> SEQ ID NO 174
<211> LENGTH: 14
<212> TYPE: PRT
<213> ORGANISM: Artificial Sequence
<220> FEATURE:
<223> OTHER INFORMATION: synthetic

<400> SEQUENCE: 174

```
Tyr Asn Gly Val Cys Cys Gly Tyr Leu Leu Cys His Pro Cys
1               5                   10
```

<210> SEQ ID NO 175
<211> LENGTH: 14
<212> TYPE: PRT
<213> ORGANISM: Artificial Sequence
<220> FEATURE:
<223> OTHER INFORMATION: synthetic

<400> SEQUENCE: 175

```
Tyr Asn Gly Val Cys Cys Gly Tyr Lys Asn Cys His Pro Cys
1               5                   10
```

<210> SEQ ID NO 176
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is L-2-furylalanine

<400> SEQUENCE: 176

```
Asn Gly Val Cys Cys Gly Xaa Lys Leu Cys His Pro Cys
1               5                   10
```

<210> SEQ ID NO 177
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 177

```
Asn Gly Val Cys Cys Gly Tyr Arg Leu Cys His Xaa Cys
1               5                   10
```

<210> SEQ ID NO 178
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: L-histidine(benzyloxymethyl)

<400> SEQUENCE: 178

```
Asn Gly Val Cys Cys Gly Tyr Lys Leu Cys Xaa Pro Cys
1               5                   10
```

<210> SEQ ID NO 179
<211> LENGTH: 14
<212> TYPE: PRT
<213> ORGANISM: Artificial Sequence
<220> FEATURE:
<223> OTHER INFORMATION: synthetic

<400> SEQUENCE: 179

Tyr Asn Gly Val Cys Cys Gly Tyr Phe Leu Cys His Pro Cys
1               5                   10

<210> SEQ ID NO 180
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: Xaa is L-histidine(3-methyl)

<400> SEQUENCE: 180

Asn Gly Val Cys Cys Gly Tyr Lys Leu Cys Xaa Pro Cys
1               5                   10

<210> SEQ ID NO 181
<211> LENGTH: 13
<212> TYPE: PRT
<213> ORGANISM: Artificial Sequence
<220> FEATURE:
<223> OTHER INFORMATION: synthetic

<400> SEQUENCE: 181

Asn Gly Val Cys Cys Gly Tyr His Leu Cys His Pro Cys
1               5                   10

<210> SEQ ID NO 182
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-pyroglutamic acid
<220> FEATURE:
<221> NAME/KEY: MISC_FEATURE
<222> LOCATION: (8)..(8)
<223> OTHER INFORMATION: Xaa is L-norleucine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 182

Xaa Gly Val Cys Cys Gly Tyr Xaa Leu Cys His Xaa Cys
1               5                   10

<210> SEQ ID NO 183
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: Xaa is D-glutamic acid

<400> SEQUENCE: 183

Asn Gly Val Cys Cys Glu Tyr Lys Leu Cys His Pro Cys
1               5                   10

<210> SEQ ID NO 184
<211> LENGTH: 14
<212> TYPE: PRT
<213> ORGANISM: Artificial Sequence
<220> FEATURE:
<223> OTHER INFORMATION: synthetic

<400> SEQUENCE: 184

Tyr Asn Gly Val Cys Cys Gly Asn Lys Leu Cys His Pro Cys
1               5                   10

<210> SEQ ID NO 185
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Xaa is L-norleucine

<400> SEQUENCE: 185

Asn Gly Val Cys Cys Gly Tyr Xaa Leu Cys His Pro Cys
1               5                   10

<210> SEQ ID NO 186
<211> LENGTH: 13
<212> TYPE: PRT
<213> ORGANISM: Artificial Sequence
<220> FEATURE:
<223> OTHER INFORMATION: synthetic

<400> SEQUENCE: 186

Asn Gly Val Cys Cys Ser Tyr Lys Leu Cys His Pro Cys
1               5                   10

<210> SEQ ID NO 187
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-pyroglutamic acid
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 187

Xaa Gly Val Cys Cys Gly Trp Lys Leu Cys His Xaa Cys
1               5                   10

<210> SEQ ID NO 188
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE

```
<222> LOCATION: (6)..(6)
<223> OTHER INFORMATION: Xaa is D-serine

<400> SEQUENCE: 188

Asn Gly Val Cys Cys Xaa Tyr Lys Leu Cys His Pro Cys
1               5                   10

<210> SEQ ID NO 189
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-pyroglutamic acid
<220> FEATURE:
<221> NAME/KEY: MISC_FEATURE
<222> LOCATION: (8)..(8)
<223> OTHER INFORMATION: Xaa is L-Citrulline
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 189

Xaa Gly Val Cys Cys Gly Tyr Xaa Leu Cys His Xaa Cys
1               5                   10

<210> SEQ ID NO 190
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 190

Asn Gly Val Cys Cys Gly Tyr Lys Leu Cys Ala Xaa Cys
1               5                   10

<210> SEQ ID NO 191
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is L-1,2,3,4-tetrahydroisoquinoline-3-
      carboxylic acid

<400> SEQUENCE: 191

Asn Gly Val Cys Cys Gly Xaa Lys Leu Cys His Pro Cys
1               5                   10

<210> SEQ ID NO 192
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: Xaa is D-phenylalanine
```

```
<400> SEQUENCE: 192

Asn Gly Val Cys Cys Xaa Tyr Lys Leu Cys His Pro Cys
1               5                   10

<210> SEQ ID NO 193
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 193

Gly Ile Cys Cys Gly Val Ser Phe Cys Tyr Xaa Cys
1               5                   10

<210> SEQ ID NO 194
<211> LENGTH: 13
<212> TYPE: PRT
<213> ORGANISM: Artificial Sequence
<220> FEATURE:
<223> OTHER INFORMATION: synthetic

<400> SEQUENCE: 194

Asn Gly Val Cys Cys Gly Tyr Gln Leu Cys His Pro Cys
1               5                   10

<210> SEQ ID NO 195
<211> LENGTH: 14
<212> TYPE: PRT
<213> ORGANISM: Artificial Sequence
<220> FEATURE:
<223> OTHER INFORMATION: synthetic

<400> SEQUENCE: 195

Tyr Asn Gly Val Cys Cys Gly Glu Lys Leu Cys His Pro Cys
1               5                   10

<210> SEQ ID NO 196
<211> LENGTH: 13
<212> TYPE: PRT
<213> ORGANISM: Artificial Sequence
<220> FEATURE:
<223> OTHER INFORMATION: synthetic

<400> SEQUENCE: 196

Asn Gly Val Cys Cys Gly Tyr Lys Lys Cys His Pro Cys
1               5                   10

<210> SEQ ID NO 197
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-pyroglutamic acid
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 197
```

Xaa Gly Val Cys Cys Gly Glu Lys Leu Cys His Xaa Cys
1               5                   10

<210> SEQ ID NO 198
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is L-pyroglutamic acid
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 198

Xaa Gly Val Cys Cys Gly Ile Lys Leu Cys His Xaa Cys
1               5                   10

<210> SEQ ID NO 199
<211> LENGTH: 11
<212> TYPE: PRT
<213> ORGANISM: Artificial Sequence
<220> FEATURE:
<223> OTHER INFORMATION: synthetic

<400> SEQUENCE: 199

Arg Asn Cys Cys Arg Leu Gln Val Cys Cys Gly
1               5                   10

<210> SEQ ID NO 200
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 200

Val Gly Val Asp Asp Gly Tyr Lys Leu Cys His Xaa Cys
1               5                   10

<210> SEQ ID NO 201
<211> LENGTH: 14
<212> TYPE: PRT
<213> ORGANISM: Artificial Sequence
<220> FEATURE:
<223> OTHER INFORMATION: synthetic

<400> SEQUENCE: 201

Tyr Asn Gly Val Cys Cys Gly Lys Lys Leu Cys His Pro Cys
1               5                   10

<210> SEQ ID NO 202
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 202

Asn Gly Val Cys Cys Gly Tyr Lys Ala Cys His Xaa Cys
1               5                   10

<210> SEQ ID NO 203
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 203

Asn Gly Val Cys Cys Gly Tyr Ala Leu Cys His Xaa Cys
1               5                   10

<210> SEQ ID NO 204
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 204

Asn Gly Val Cys Cys Gly Ala Lys Leu Cys His Xaa Cys
1               5                   10

<210> SEQ ID NO 205
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 205

Asn Gly Val Cys Cys Ala Tyr Lys Leu Cys His Xaa Cys
1               5                   10

<210> SEQ ID NO 206
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)

```
<223> OTHER INFORMATION: Xaa is L-dimethyldopa or
      L-dimethoxyphenylalanine

<400> SEQUENCE: 206

Asn Gly Val Cys Cys Gly Xaa Lys Leu Cys His Pro Cys
1               5                   10

<210> SEQ ID NO 207
<211> LENGTH: 14
<212> TYPE: PRT
<213> ORGANISM: Artificial Sequence
<220> FEATURE:
<223> OTHER INFORMATION: synthetic

<400> SEQUENCE: 207

Tyr Asn Gly Val Cys Cys Gly Tyr Lys Leu Cys Arg Pro Cys
1               5                   10

<210> SEQ ID NO 208
<211> LENGTH: 14
<212> TYPE: PRT
<213> ORGANISM: Artificial Sequence
<220> FEATURE:
<223> OTHER INFORMATION: synthetic

<400> SEQUENCE: 208

Tyr Asn Gly Val Cys Cys Gly Tyr Ile Leu Cys His Pro Cys
1               5                   10

<210> SEQ ID NO 209
<211> LENGTH: 14
<212> TYPE: PRT
<213> ORGANISM: Artificial Sequence
<220> FEATURE:
<223> OTHER INFORMATION: synthetic

<400> SEQUENCE: 209

Tyr Asn Gly Val Cys Cys Gly Tyr Lys Asp Cys His Pro Cys
1               5                   10

<210> SEQ ID NO 210
<211> LENGTH: 14
<212> TYPE: PRT
<213> ORGANISM: Artificial Sequence
<220> FEATURE:
<223> OTHER INFORMATION: synthetic

<400> SEQUENCE: 210

Tyr Asn Gly Val Cys Cys Gly Tyr Lys Leu Cys Glu Pro Cys
1               5                   10

<210> SEQ ID NO 211
<211> LENGTH: 14
<212> TYPE: PRT
<213> ORGANISM: Artificial Sequence
<220> FEATURE:
<223> OTHER INFORMATION: synthetic

<400> SEQUENCE: 211

Tyr Asn Gly Val Cys Cys Gly Tyr Trp Leu Cys His Pro Cys
1               5                   10

<210> SEQ ID NO 212
<211> LENGTH: 14
<212> TYPE: PRT
<213> ORGANISM: Artificial Sequence
<220> FEATURE:
```

-continued

<223> OTHER INFORMATION: synthetic

<400> SEQUENCE: 212

Tyr Asn Gly Val Cys Cys Gly Tyr Tyr Leu Cys His Pro Cys
1               5                   10

<210> SEQ ID NO 213
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is L-dimethyldopa or
      L-dimethoxyphenylalanine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 213

Asn Gly Val Cys Cys Gly Xaa Lys Leu Cys His Xaa Cys
1               5                   10

<210> SEQ ID NO 214
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is L-Diphenylalanine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 214

Asn Gly Val Cys Cys Gly Xaa Lys Leu Cys His Xaa Cys
1               5                   10

<210> SEQ ID NO 215
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is L-Lysine (dimethyl)
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 215

Asn Gly Val Cys Cys Gly Xaa Lys Leu Cys His Xaa Cys
1               5                   10

The invention claimed is:

1. An isolated, synthetic or recombinant χ-conotoxin peptide having the ability to inhibit a neuronal noradrenaline transporter comprising the following sequence of amino acids:

```
                                        (SEQ ID NO. 3)
     Cys Cys Gly Tyr Lys Leu Cys Xaa5 Xaa6 Cys
``` wherein the peptide has one disulfide bond between the cysteines at positions 1 and 10 of SEQ ID NO: 3 and a second disulfide bond between the cysteines at positions 2 and 7 of SEQ ID NO: 3, where Xaa5 and Xaa6 represent any amino acid residue except Cys; or a sequence in which at least one of Tyr or Leu is subject to side chain modification, wherein said side chain modification for Tyr is a substitution of Tyr with MeY, and said side chain modification for Leu is a substitution of Leu with Hle or Nle; with the proviso that the peptide is not χ-MrIA, χ-MrIB, Mar2, CMrVIA, Bn1.5, Mr1.3 or Au1.4;

or a salt, ester, amide, prodrug or cyclised derivative thereof.

2. The χ-conotoxin peptide according to claim 1 comprising the following sequence of amino acids:

```
Xaa1 Xaa2 Xaa3 Xaa4 Cys Cys Gly Tyr Lys Leu Cys Xaa5 Xaa6 Cys   (SEQ ID NO.
                                                                   5)
``` wherein the peptide has one disulfide bond between the cysteines at positions 4 and 13 of SEQ ID NO: 5 and a second disulfide bond between the cysteines at positions 5 and 10 of SEQ ID NO: 5, where Xaa1 is an N-terminal residue and is either pGlu or DpGlu;
Xaa2 is a deletion,
Xaa3 is Gly,
Xaa4 is Val, and
Xaa5 and Xaa6 represent any amino acid residue except Cys;
or such a sequence where at least one of Tyr or Leu is subject to side-chain modification, wherein said side chain modification for Tyr is a substitution of Tyr with MeY, and said side chain modification for Leu is a substitution of Leu with Hle or Nle, or a salt, ester, amide or prodrug thereof.

3. The χ-conotoxin peptide according to claim 2 consisting of the following sequence of amino acids:

```
Xaa1 Xaa2 Xaa3 Xaa4 Cys Cys Gly Tyr Lys Leu Cys Xaa5 Xaa6 Cys   SEQ ID NO. 5
``` wherein the peptide has one disulfide bond between the cysteines at positions 4 and 13 of SEQ ID NO: 5 and a second disulfide bond between the cysteines at positions 5 and 10 of SEQ ID NO: 5, where Xaa1 is an N-terminal residue and is either pGlu or DpGlu;
Xaa2 is a deletion,
Xaa3 is Gly,
Xaa4 is Val, and
Xaa5 and Xaa6 represent any amino acid residue except Cys;
or such a sequence where at least one of Tyr or Leu is subject to side chain modification, wherein said side chain modification for Tyr is a substitution of Tyr with MeY, and said side chain modification for Leu is a substitution of Leu with Hle or Nle, or a salt, ester, amide or pro drug thereof.

4. The peptide according to claim 1 wherein the Tyr has been replaced with MeY and/or the Leu is replaced with Hle or Nle.

5. The peptide according to claim 2 wherein the Tyr residue has been replaced with MeY and/or the Leu residue is replaced with Hle or Nle.

6. The peptide according to claim 1 consisting of from 11 to 20 amino acids.

7. A composition comprising an isolated, synthetic or recombinant χ-conotoxin peptide having the ability to inhibit a neuronal noradrenaline transporter, wherein said χ-conotoxin peptide comprises the following sequence of amino acids:

```
              Cys Cys Gly Tyr Lys Leu Cys Xaa5 Xaa6 Cys    (SEQ ID NO. 3)
``` wherein the peptide has one disulfide bond between the cysteines at positions 1 and 10 of SEQ ID NO: 3 and a second disulfide bond between the cysteines at positions 2 and 7 of SEQ ID NO: 3, where Xaa5 and Xaa6 represent any amino acid residue except Cys, or such a sequence in which at least one of Tyr or Leu is subject to side chain modification, wherein said side chain modification for Tyr is a substitution of Tyr with MeY, and said side chain modification for Leu is a substitution of Leu with Hle or Nle, with the proviso that the peptide is not χ-MrIA, χ-MrIB, Mar2, CMrVIA, Bn1.5, Mr1.3 or Au1.4; or a salt, ester, amide, prodrug or cyclised derivative thereof,
and a pharmaceutically acceptable carrier or diluent.

8. The peptide according to claim 2, wherein Xaa5 is selected from the group consisting of His, Arg, Trp, Nal, and Glu.

9. The peptide according to claim 2, wherein Xaa5 is Arg or His.

10. The peptide according to claim 2, wherein Xaa6 is selected from the group consisting of Hyp, Pro, Ala, Tic, Pip, MeY, DMD, Phe, THZ, Glu, Nle, and Tyr.

11. The peptide according to claim 10, wherein Xaa6 is Hyp or Pro.

12. The peptide according to claim 1, 2, or 3, wherein Xaa5 is selected from the group consisting of His, Arg, Trp, Nal and Glu.

13. The peptide according to claim 12 wherein Xaa5 is Arg or His.

14. The peptide according to claim 1, 2 or 3, wherein Xaa6 is selected from the group consisting of Hyp, Pro, Ala, Tic, Pip, MeY, DMD, Phe, THZ, Glu, Nle, and Tyr.

15. The peptide according to claim 14 wherein Xaa6 is Hyp or Pro.

16. The peptide of claim 2 consisting of 13 to 20 amino acids.

* * * * *